United States Patent
Hirota

(10) Patent No.: US 10,356,378 B2
(45) Date of Patent: Jul. 16, 2019

(54) IMAGE PROCESSING DEVICE, IMAGE PROCESSING METHOD, AND COMPUTER-READABLE RECORDING MEDIUM

(71) Applicant: OLYMPUS CORPORATION, Tokyo (JP)

(72) Inventor: Masashi Hirota, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/813,626

(22) Filed: Nov. 15, 2017

(65) Prior Publication Data

US 2018/0077399 A1    Mar. 15, 2018

Related U.S. Application Data

(63) Continuation of application No. PCT/JP2016/052330, filed on Jan. 27, 2016.

(30) Foreign Application Priority Data

May 21, 2015 (WO) .................. PCT/JP2015/064651

(51) Int. Cl.
*G06T 7/00* (2017.01)
*H04N 9/76* (2006.01)
(Continued)

(52) U.S. Cl.
CPC .......... *H04N 9/76* (2013.01); *A61B 1/00009* (2013.01); *A61B 1/04* (2013.01); *G06T 5/50* (2013.01);
(Continued)

(58) Field of Classification Search
None
See application file for complete search history.

(56) References Cited

U.S. PATENT DOCUMENTS

2009/0141125 A1* 6/2009 Yamazaki ............ A61B 1/0638
348/70
2012/0154565 A1* 6/2012 Kaku .................. A61B 1/00009
348/68

(Continued)

FOREIGN PATENT DOCUMENTS

JP    2005198794 A    7/2005
JP    2008036035 A    2/2008

(Continued)

OTHER PUBLICATIONS

International Search Report dated Apr. 12, 2016 issued in PCT/JP2016/052330.

*Primary Examiner* — Delomia L Gilliard
(74) *Attorney, Agent, or Firm* — Scully, Scott, Murphy & Presser, P.C.

(57) ABSTRACT

An image processing device includes: an image acquisition unit configured to acquire images including at least one narrow-band image and having different wavelength component distributions from one another; an absorption information extracting unit configured to extract absorption information from a first image on the basis of a specific frequency component in the first image and correlation between the first image and a second image, the first image being a narrow-band image among the images, the second image being an image different from the first image among the images, the absorption information being image information indicating a change in absorption caused by absorption of narrow-band light used in capturing of the first image by a light absorber; and a display image generating unit configured to generate an image for display by combining the absorption information with at least any one of the images.

23 Claims, 17 Drawing Sheets

(51) Int. Cl.
*A61B 1/04* (2006.01)
*G06T 5/50* (2006.01)
*H04N 9/083* (2006.01)
*A61B 1/00* (2006.01)
*A61B 1/06* (2006.01)

(52) U.S. Cl.
CPC ........... *G06T 7/0014* (2013.01); *H04N 9/083* (2013.01); *A61B 1/0638* (2013.01); *G06T 2207/10024* (2013.01); *G06T 2207/10068* (2013.01); *G06T 2207/20224* (2013.01); *G06T 2207/30196* (2013.01)

(56) References Cited

U.S. PATENT DOCUMENTS

| | | | |
|---|---|---|---|
| 2012/0154566 A1* | 6/2012 | Kaku | G02B 23/26 348/68 |
| 2012/0257029 A1* | 10/2012 | Igarashi | A61B 1/00009 348/68 |
| 2012/0302847 A1* | 11/2012 | Ozawa | A61B 1/00009 600/339 |
| 2012/0327205 A1 | 12/2012 | Takahashi | |
| 2013/0197371 A1* | 8/2013 | Chiba | A61B 1/0638 600/476 |
| 2015/0363932 A1* | 12/2015 | Hirota | G06T 5/003 382/128 |
| 2016/0183774 A1* | 6/2016 | Shiraishi | A61B 1/00009 600/317 |

FOREIGN PATENT DOCUMENTS

| | | |
|---|---|---|
| JP | 2011135983 A | 7/2011 |
| JP | 2012080939 A | 4/2012 |
| JP | 2012125461 A | 7/2012 |
| JP | 2012125462 A | 7/2012 |
| JP | 2012239816 A | 12/2012 |
| JP | 2014161627 A | 9/2014 |
| JP | 2014212925 A | 11/2014 |
| JP | 2015066127 A | 4/2015 |
| WO | 2012081297 A1 | 6/2012 |

* cited by examiner

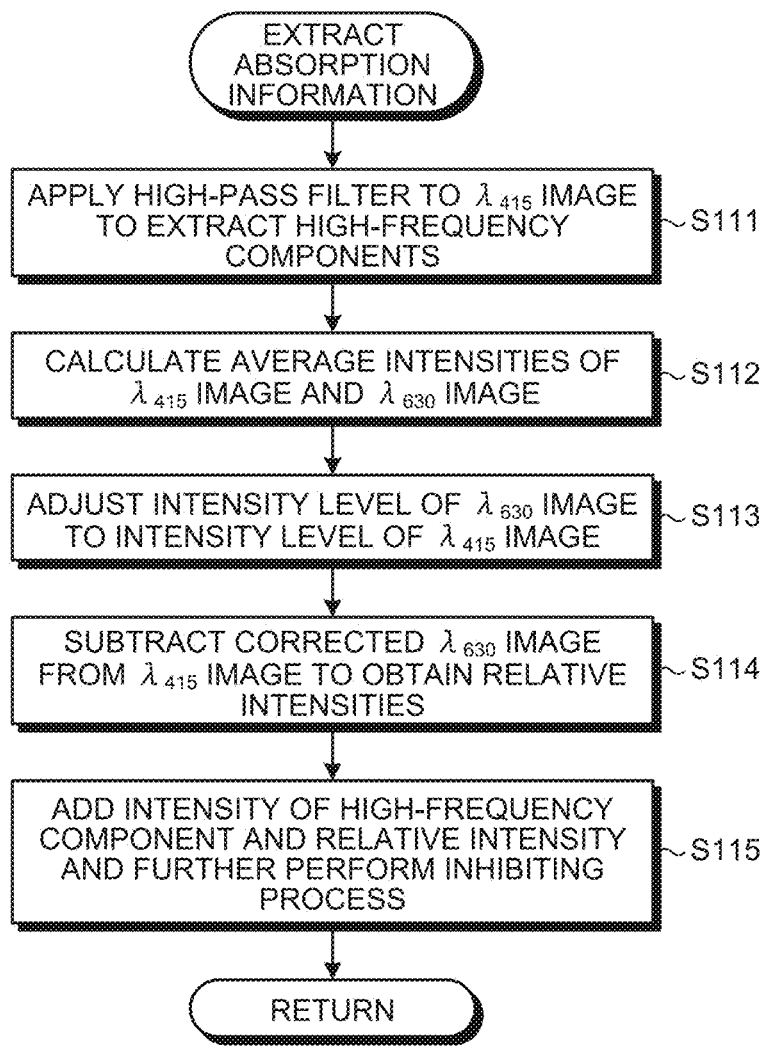

IMAGE PROCESSING DEVICE, IMAGE PROCESSING METHOD, AND COMPUTER-READABLE RECORDING MEDIUM

CROSS-REFERENCE TO RELATED APPLICATION

This application is a continuation of PCT international application Ser. No. PCT/JP2016/052330, filed on Jan. 27, 2016 which designates the United States, incorporated herein by reference, and which claims the benefit of priority from International Application No. PCT/JP2015/064651, filed on May 21, 2015, incorporated herein by reference.

BACKGROUND

The present disclosure relates to an image processing device, an image processing method, and a computer-readable recording medium.

White light and narrow-band light are used for illumination light for illuminating the inside of a living body with an endoscope. Narrow-band light has different absorption/scattering characteristics depending on the wavelength band, and features of a subject depending on the wavelength band may thus be extracted by appropriately selecting narrow-band light to be used. For example, since blue narrow-band light is easily absorbed by hemoglobin, fine blood vessels on a superficial layer under a mucosa or the like clearly appear in a narrow-band image captured with use of blue narrow-band light. Changes in absorption occurring at the subject depending on such absorption/scattering characteristics of narrow-band light hardly appear in a white image captured with white light. Thus, generation of an image having features of both of a narrow-band image and a white image allows more detailed endoscopic observation.

For example, JP 2012-125461 A discloses combining an image captured with white light with an image obtained by applying frequency filtering to an image captured with white light to generate an image having features of both of the images.

SUMMARY

An image processing device according to the one aspect of the present disclosure includes: an image acquisition unit configured to acquire a plurality of images including at least one narrow-band image and having different wavelength component distributions from one another; an absorption information extracting unit configured to extract absorption information from a first image on the basis of a specific frequency component in the first image and correlation between the first image and a second image, the first image being a narrow-band image among the plurality of images, the second image being an image different from the first image among the plurality of images, the absorption information being image information indicating a change in absorption caused by absorption of narrow-band light used in capturing of the first image by a light absorber; and a display image generating unit configured to generate an image for display by combining the absorption information with at least any one of the plurality of images.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a flowchart illustrating a process of extracting absorption information in the first embodiment;

DETAILED DESCRIPTION

An image processing device, an image processing method, and an image processing program according to embodiments will now be described with reference to the drawings. Note that the present disclosure is not limited to

First Embodiment

Figure 1:
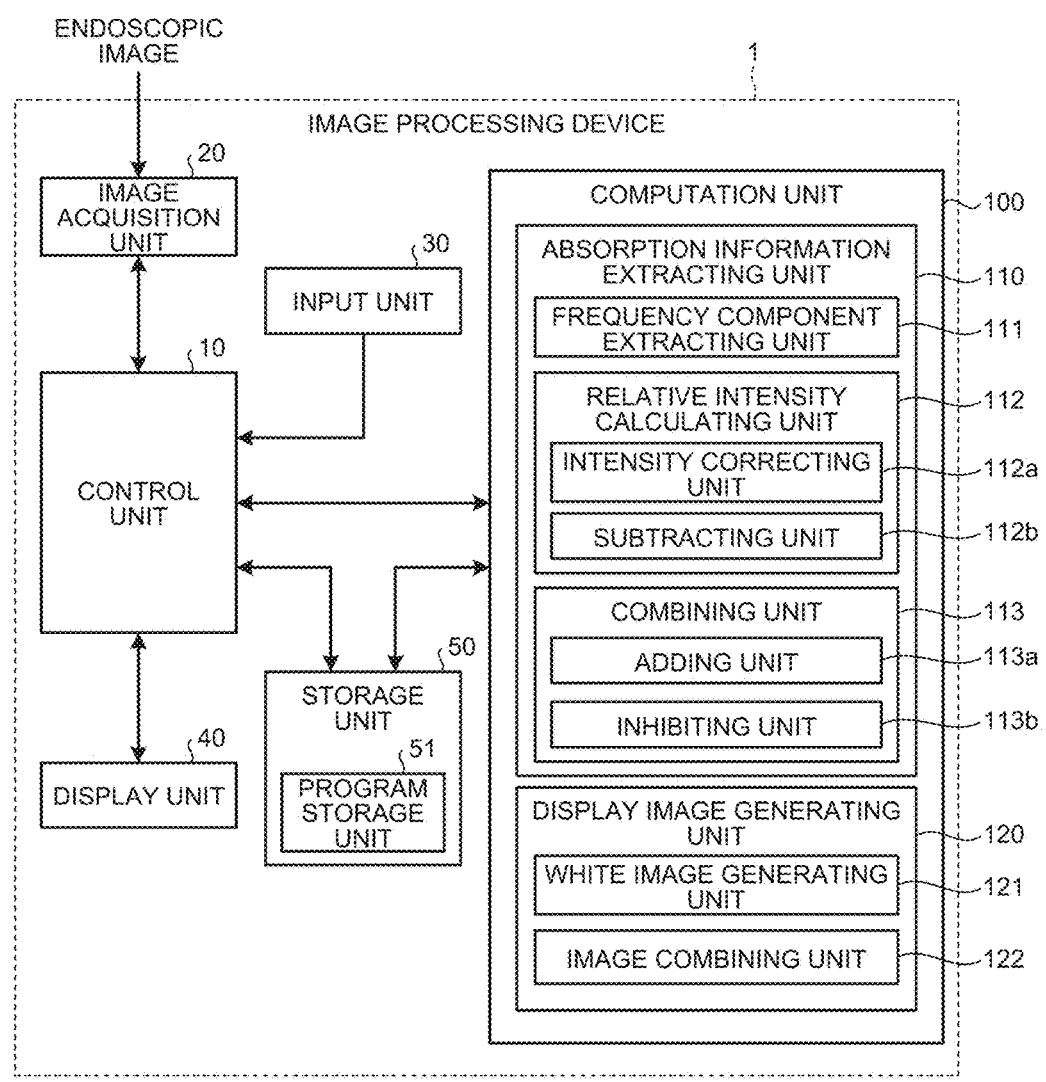
FIG. 1 is a block diagram illustrating a configuration of an image processing device according to a first embodiment.

FIG. 1 is a block diagram illustrating a configuration of an image processing device according to a first embodiment. An image processing device 1 according to the first embodiment is a device configured to extract changes in absorption, which hardly appear in a white image, on the basis of a plurality of images acquired by an endoscope and combine the extracted changes in absorption with one or more images to generate an image for display.

In the description below, endoscopic images including narrow-band images and white images acquired by capturing the inside of lumens of living bodies by a typical endoscope called videoscope or a capsule endoscope are processed.

As illustrated in FIG. 1, the image processing device 1 includes a control unit 10 configured to control overall operation of the image processing device 1, an image acquisition unit 20 configured to acquire image data of endoscopic images, an input unit 30 configured to generate input signals based on external operations, a display unit 40 configured to provide various displays, a storage unit 50 configured to store image data acquired by the image acquisition unit 20 and various programs, and a computation unit 100 configured to perform predetermined image processing on image data.

The control unit 10 is constituted by a general-purpose processor such as a central processing unit (CPU) or a special-purpose processor such as various computation circuits configured to perform specific functions such as an application specific integrated circuit (ASIC). In a case where the control unit 10 is a general-purpose processor, the control unit 10 provides instructions, transfers data, and the like to respective components of the image processing device 1 by reading various programs stored in the storage unit 50 to generally control the overall operation of the image processing device 1. In a case where the control unit 10 is a special-purpose processor, the processor may perform various processes alone or may use various data and the like stored in the storage unit 50 so that the processor and the storage unit 50 perform various processes in cooperation or in combination.

The image acquisition unit 20 is suitably configured depending on the mode of a system including the endoscope. For example, in a case where the image processing device 1 is connected to a typical endoscope system in which a videoscope is inserted into a body, the image acquisition unit 20 is constituted by an interface for loading image data generated by the endoscope system. Alternatively, in a case where a server for saving image data generated by the endoscope system is provided, the image acquisition unit 20 is constituted by a communication device or the like connected with the server, and acquires image data through data communication with the server. Alternatively, in a case where a capsule endoscope that performs capturing while moving in a living body is used, image data may be delivered on a portable storage medium to/from the capsule endoscope, and in this case, the image acquisition unit 20 is constituted by a reader device on which a portable storage medium is removably mounted and which reads image data of images stored in the storage medium.

The input unit 30 is constituted by input devices such as a keyboard, a mouse, a touch panel, and various switches, for example, and outputs input signals, which are generated depending on external operation to the input devices, to the control unit 10.

The display unit 40 is constituted by a display device such as an LCD or an EL display, and displays various screens including endoscopic images under the control of the control unit 10.

The storage unit 50 is constituted by various IC memories such as a ROM or a RAM such as an updatable flash memory, an information storage device such as a hard disk or a CD-ROM that is built in or connected via a data communication terminal, a writing/reading device that reads/writes information from/to the information storage device, and the like. The storage unit 50 stores programs for making the image processing device 1 operate and for making the image processing device 1 perform various functions, data used in execution of the programs, and the like in addition to image data of endoscopic images acquired by the image acquisition unit 20. Specifically, the storage unit 50 includes a program storage unit 51 that stores image processing programs for making the image processing device 1 perform image processing to generate an image for display obtained by combining changes in absorption extracted from at least one narrow-band image acquired by the endoscope with another image on the basis of a plurality of images having different wavelength component distributions and including the narrow-band image.

The computation unit 100 is constituted by a general-purpose processor such as a CPU or a special-purpose processor such as various computation circuits for performing specific functions such as an ASIC. In a case where the computation unit 100 is a general-purpose processor, the computation unit 100 reads an image processing program stored in the program storage unit 51 so as to perform image processing to generate an image for display obtained by combining changes in absorption extracted from at least one narrow-band image acquired by the endoscope with another image on the basis of a plurality of images having different wavelength component distributions and including the narrow-band image. Alternatively, in a case where the computation unit 100 is a special-purpose processor, the processor may perform various processes alone or may use various data and the like stored in the storage unit 50 so that the processor and the storage unit 50 perform image processing in cooperation or in combination.

Next, a configuration of the computation unit 100 will be described. As illustrated in FIG. 1, the computation unit 100 includes an absorption information extracting unit 110 configured to extract absorption information from a plurality of image acquired by the image acquisition unit 20, and a display image generating unit 120 configured to generate an image for display obtained by combining the extracted absorption information with an image. In the following, a process in a case where a plurality of narrow-band images having different center wavelengths from one another are acquired will be described as an example.

Note that absorption information refers to image information indicating changes in absorption appearing in a narrow-band image as a result of narrow-band light used for capturing the narrow-band image being absorbed by a light absorber inside a subject. The changes in absorption appearing in a narrow-band image vary depending on the absorption/scattering characteristics of the narrow-band light. For example, since narrow-band light having a center wavelength of about 415 nm is easily absorbed by hemoglobin, changes in absorption appear in a narrow-band image as a result of an increase in the amount of absorption of the narrow-band light in blood vessels through which blood containing hemoglobin flows or in vascular proliferation regions. The pixel positions of the regions in which the absorption has changed and values indicating the amounts of change in the absorption of the narrow-band light at the pixel positions are included in the absorption information. Since the narrow-band light is absorbed and the brightness is lowered in a region in which the absorption has changed, the value indicating the amount of change in the absorption is a negative value. The value indicating the amount of change in the absorption is smaller as the amount of narrow-band light absorbed by the light absorber is larger. In other words, the absolute value is larger.

The absorption information extracting unit 110 extracts absorption information appearing in a narrow-band image on the basis of the absorption/scattering characteristics of narrow-band light. Specifically, narrow-band light having a center wavelength of about 415 nm has characteristics of being easily absorbed by hemoglobin and being easily scattered in a mucosa inside a lumen. Conversely, narrow-band light having a center wavelength of about 630 nm has characteristics of being hardly absorbed by hemoglobin and being hardly scattered in a mucosa, and thus easily reaching deep into a lumen. The absorption information extracting unit 110 extracts image information, as the absorption information, such as a regional change in absorption caused by fine blood vessels on a superficial layer under a mucosa or vascular proliferation from a narrow-band image on the basis of the difference in the characteristics of narrow-band light. Hereinafter, a narrow-band image from which the absorption information is acquired will be referred to as a specific narrow-band image.

The absorption information extracting unit 110 includes a frequency component extracting unit 111, a relative intensity calculating unit 112, and a combining unit 113. The frequency component extracting unit 111 applies a high-pass filter to a specific narrow-band image (first image) to generate a high-frequency component image obtained by extracting a high-frequency component as a specific frequency component.

The relative intensity calculating unit 112 calculates a relative intensity between a plurality of narrow-band images. Specifically, the relative intensity calculating unit 112 calculates a relative intensity between a narrow-band image (second image) and the specific narrow-band image, the narrow-band image being captured with narrow-band light with the smallest amount absorbed by the light absorber appearing in a specific narrow-band image among a plurality of narrow-band images other than the specific narrow-band image, that is, more specifically, narrow-band light having a center wavelength of about 630 nm. Hereinafter, the narrow-band image captured with narrow-band light with the smallest amount absorbed by the light absorber will be referred to as a low-absorption image. The relative intensity calculating unit 112 includes an intensity correcting unit 112a configured to correct the intensity of the low-absorption image to that of the specific narrow-band image, and a subtracting unit 112b configured to subtract the corrected intensity of the low-absorption image from the intensity of the specific narrow-band image to obtain a relative intensity between the images.

The combining unit 113 exhaustively acquires absorption information appearing in the specific narrow-band image on the basis of the intensity of the high-frequency component extracted by the frequency component extracting unit 111 and the relative intensity calculated by the relative intensity calculating unit 112. More specifically, the combining unit 113 includes an adding unit 113a configured to add the intensity of the high-frequency component and the relative intensity at the same pixel position, and an inhibiting unit 113b configured to inhibit an output value depending on the addition result.

The display image generating unit 120 includes a white image generating unit 121 configure to generate a while image from a plurality of narrow-band images, and an image combining unit 122 configured to combine the absorption information extracted by the absorption information extracting unit 110 with the white image.

Figure 2:
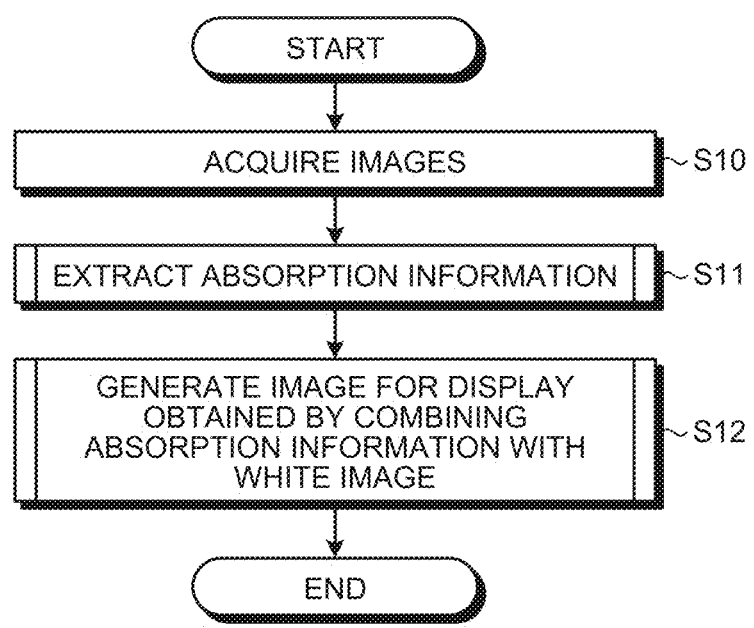
FIG. 2 is a flowchart illustrating operation of the image processing device illustrated in FIG. 1.

Next, operation of the image processing device 1 will be described. FIG. 2 is a flowchart illustrating the operation of the image processing device 1. First, in step S10, the image acquisition unit 20 acquires a plurality of images including at least two narrow-band images having different center wavelengths from each other. Note that the images include images corresponding to respective wavelength bands of R, G, and B. Specifically, a narrow-band image having a center wavelength of 415 nm from which absorption information is to be extracted, and three narrow-band images having center wavelengths of 460 nm, 540 nm, and 630 nm corresponding to the wavelength bands of R, G, and B, respectively, are acquired. Alternatively, a narrow-band image having a center wavelength of 415 nm from which absorption information is to be extracted, a narrow-band image having a center wavelength of 630 nm corresponding to a wavelength band whose amount absorbed by a light absorber that absorbs narrow-band light with a center wavelength of 415 nm is small, and a white image including the wavelength bands of R, G, and B may be acquired. In the first embodiment, assume that the former four narrow-band images are acquired.

The method by which the narrow-band images are acquired is not particularly limited. An example of the method for acquiring narrow-band images by an endoscope is a method of using a plurality of LEDs for emitting light rays having narrow-band peak wavelengths. For example, LEDs for emitting light rays having peaks with centers at wavelengths 460 nm, 540 nm, and 630 nm corresponding to wavelength bands of R, G, and B, and an LED for emitting a light ray having a peak with a center at a wavelength 415 nm are provided on an endoscope, the LEDs are caused to emit light alternately to irradiate the inside of a living body, and a R (red) component, a G (green) component, and a B (blue) component of light reflected from the inside of the living body are respectively acquired by color image sensors. As a result, four kinds of narrow-band images respectively having center wavelengths of 415 nm, 460 nm, 540 nm, and 630 nm are acquired.

Alternatively, other examples of the method for acquiring narrow-band images include a method of providing a narrow-band pass filter in front of a while light source such as a xenon lamp and sequentially irradiating the inside of a living body with narrow-band light obtained by the narrow-band pass filter, and a method of sequentially driving a plurality of laser diodes for emitting narrow-band light rays having different center wavelengths from one another. Still alternatively, narrow-band images may be acquired in such a manner that the inside of a living body is irradiated with white light and light reflected from the living body is made to enter image sensors via a narrow-band pass filter.

In the following, narrow-band images having center wavelengths of 415 nm, 460 nm, 540 nm, and 630 nm will be referred to as a $\lambda_{415}$ image, a $\lambda_{460}$ image, a $\lambda_{540}$ image, and a $\lambda_{630}$ image, respectively. Note that the actual center wavelengths of the narrow-band light rays with which the narrow-band images are acquired may have values close to 415 nm, 460 nm, 540 nm, and 630 nm.

Figure 3:
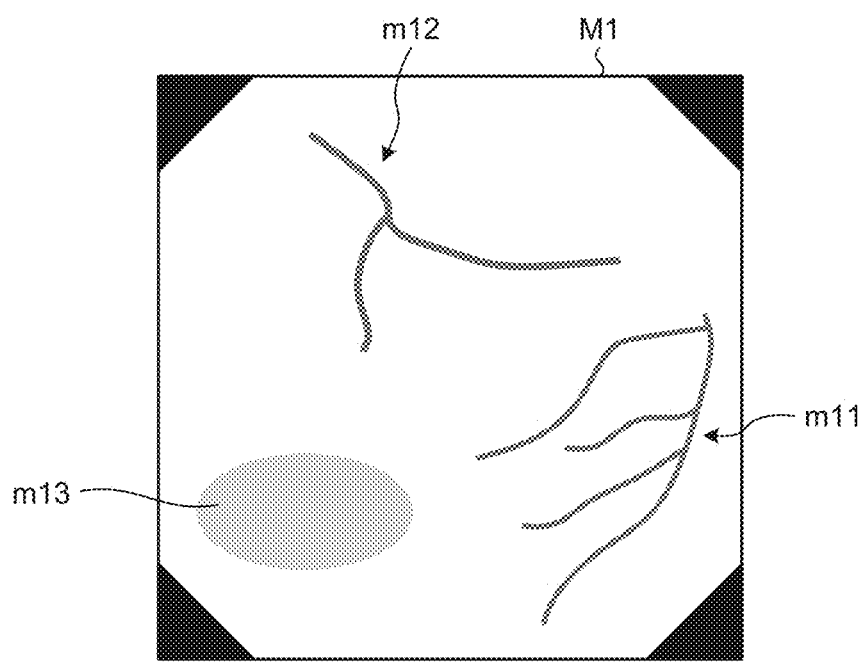
FIG. 3 is a schematic view illustrating a $\lambda_{415}$ image.

In subsequent step S11, the absorption information extracting unit 110 extracts absorption information from the $\lambda_{415}$ image. FIG. 3 is a schematic view illustrating the $\lambda_{415}$ image. In the $\lambda_{415}$ image M1 illustrated in FIG. 3, changes in absorption due to fine blood vessels m11 and slightly thicker blood vessels m12 present from a superficial layer under a mucosa to a middle layer and an absorption change region m13 in which a change in absorption due to vascular proliferation appears regionally are observed. In the first embodiment, image information indicating these changes in absorption is extracted as absorption information.

FIG. 4 is a flowchart illustrating a process of extracting the absorption information in step S11. In addition, FIGS. 5A and 5B are schematic views for explaining the process of extracting the absorption information.

In step S111, the frequency component extracting unit 111 applies a high-pass filter to the $\lambda_{415}$ image to extract high-frequency components. The pixel position of a high-frequency component whose intensity is a negative value among the extracted high-frequency components corresponds to a region in which a change in absorption of narrow-band light occurs, and the intensity of the high-frequency component represents the amount of change in absorption.

Figure 5A:
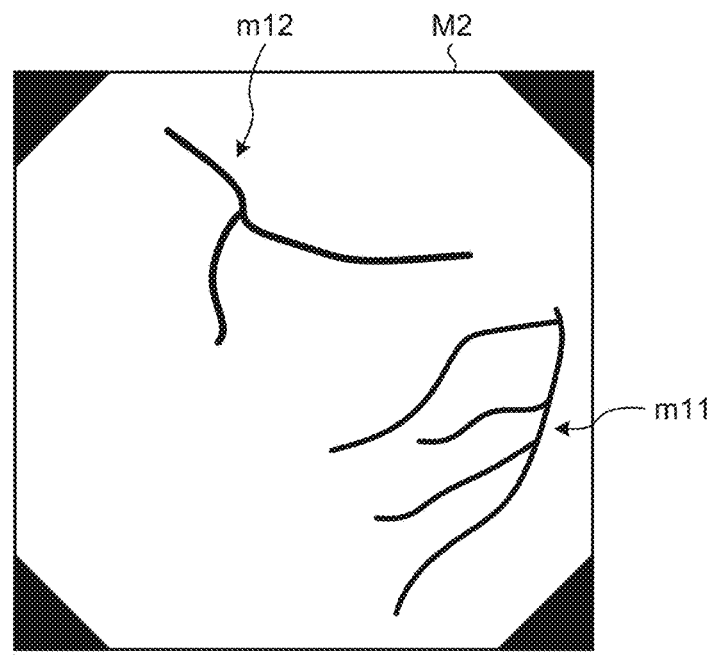
FIG. 5A is a schematic view illustrating a high-frequency component image.
Figure 5B:
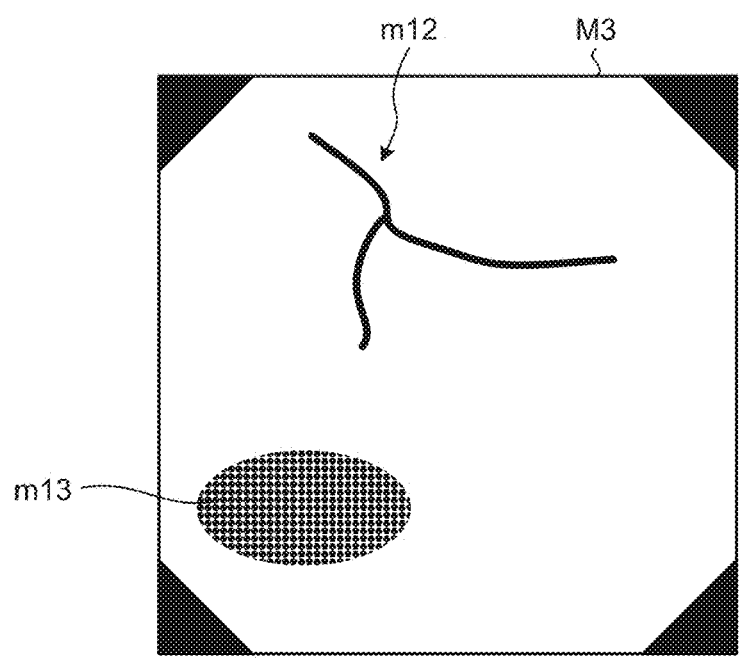
FIG. 5B is a schematic view illustrating a relative intensity image.

An image M2 illustrated in FIG. 5A is a high-frequency component image generated from a high-frequency component extracted by the high-pass filtering. As illustrated in FIG. 5A, when a high-pass filter is applied, relatively fine changes in absorption as those of the fine blood vessels m11 and the slightly thicker blood vessels m12 are easily extracted from the $\lambda_{415}$ image, but regional, that is, less fine changes in absorption as that of the absorption change region m13 (see FIG. 3) are hardly extracted.

Thus, in next step S112 and subsequent steps, the characteristics of narrow-band light with a center wavelength of 630 nm being hardly absorbed by hemoglobin is used, so that an intensity change of the $\lambda_{415}$ image relative to that of the $\lambda_{630}$ image is extracted as a change in absorption.

In step S112, the relative intensity calculating unit 112 calculates average intensities of the $\lambda_{415}$ image and the $\lambda_{630}$ image. Thus, an average value $\text{Avg}_{415}$ of pixel values of pixels in the $\lambda_{415}$ image and an average value $\text{Avg}_{630}$ of pixel values of pixels in the $\lambda_{630}$ image are calculated. Note that the pixels whose pixel values are acquired may be all the pixels in each image or pixels in a predetermined region of interest.

In subsequent step S113, the intensity correcting unit 112a integrates a ratio of the average values $\text{Avg}_{415}/\text{Avg}_{630}$ with the pixel values of respective pixels in the $\lambda_{630}$ image to perform correction to adjust the intensity level of the $\lambda_{630}$ image to that of the $\lambda_{415}$ image.

In subsequent step S114, the subtracting unit 112b subtracts the corrected $\lambda_{630}$ image from the $\lambda_{415}$ image to obtain relative intensities. More specifically, the pixel values of pixels in the corrected $\lambda_{630}$ image are subtracted from the pixel values of pixels in the $\lambda_{415}$ image at the same pixel positions. Pixel positions where the intensities have negative values among the thus obtained relative intensities correspond to a region where changes in absorption of narrow-band light have occurred, and the relative intensities represent the amounts of change in absorption.

An image M3 illustrated in FIG. 5B is a relative intensity image generated on the basis of the relative intensities obtained by subtracting the corrected $\lambda_{630}$ image from the $\lambda_{415}$ image. As illustrated in FIG. 5B, in the relative intensity image, less fine changes in absorption as those of the slightly thicker blood vessels m12 and the absorption change region m13 are easily extracted while fine changes in absorption as that of the fine blood vessels m11 (see FIG. 5A) are hardly extracted. This is because, as a result of the subtraction of the corrected $\lambda_{630}$ image from the $\lambda_{415}$ image, structures such as mucosas that are close in intensity level are offset, and the intensity in the corrected $\lambda_{630}$ image may partially become smaller than that in the $\lambda_{415}$ image owing to variation in the intensity in the $\lambda_{630}$ image and fine changes in absorption in the $\lambda_{415}$ image are likely to be offset in such parts.

Thus, in subsequent step S115, the combining unit 113 adds the intensity of the high-frequency component extracted from the $\lambda_{415}$ image and the relative intensity of the $\lambda_{415}$ image and the $\lambda_{630}$ image, and further performs an inhibiting process. Specifically, the absorption information in the $\lambda_{415}$ image is exhaustively extracted in such a manner that the intensities of high-frequency components and the relative intensities at the same pixel positions of the high-frequency component image illustrated in FIG. 5A and the relative intensity image illustrated in FIG. 5B are added.

In this case, changes in absorption that are extracted as high-frequency components and also extracted as relative intensities as those of the slightly thicker blood vessels m12 are thus doubly extracted as a result of the addition of the intensities of the high-frequency components and the relative intensities. As described above, since the value indicating the amount of change in absorption is a negative value, an inhibiting process is performed so that a negative value of the addition result will not be too large so, as to prevent double extraction of a change in absorption.

Figure 6:
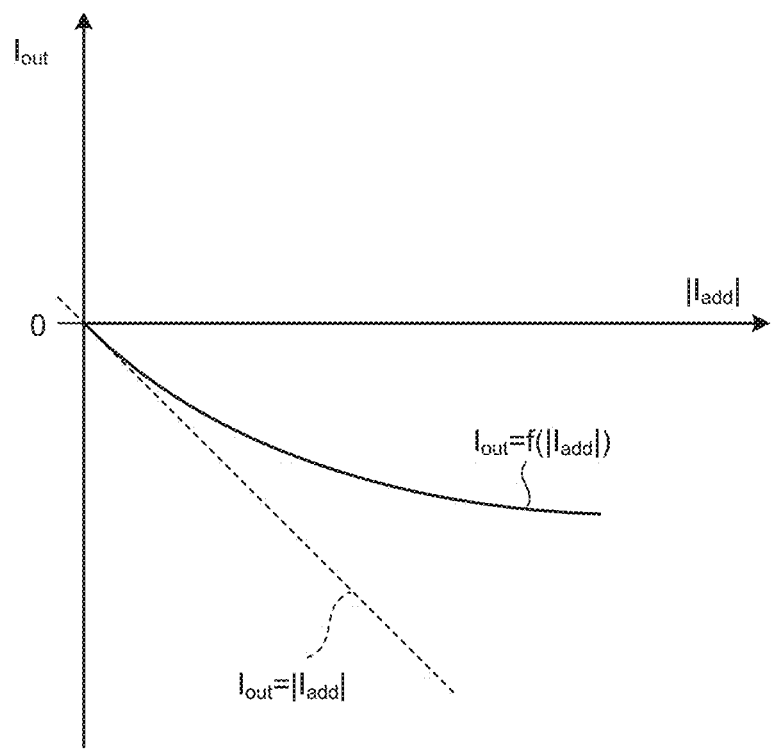
FIG. 6 is a graph illustrating an example of an inhibitory function.

Specifically, as illustrated in FIG. 6, an inhibitory function $I_{out}=f(|I_{add}|)$ for inhibiting a negative output value $I_{out}$ further as the absolute value $|I_{add}|$ is larger is applied to the addition value $I_{add}$ resulting from the addition of the intensity of a high-frequency component and the relative intensity at the same pixel positions. The addition value resulting from the inhibiting process is output as the absorption information extracted from the $\lambda_{415}$ image. Thereafter, the process returns to the main routine.

In step S12 subsequent to step S11, the display image generating unit 120 generates an image for display obtained by combining the absorption information with a white image. More specifically, the white image generating unit 121 first generates a white image by using $\lambda_{460}$ image, the $\lambda_{540}$ image, and the $\lambda_{630}$ image respectively corresponding to the wavelength bands of R, G, and B acquired in step S10. In other words, the pixel values of the respective pixels in the white image are determined by using the $\lambda_{460}$ image for B components, the $\lambda_{540}$ image for G components, and the $\lambda_{630}$ image for R components. The absorption information acquired in step S11 is then combined as a B component with the white image. Note that the method for combining the absorption information is not limited thereto; for example, the absorption information may be combined as a G component. In addition, if a white image itself is acquired in step S10, the absorption information may be directly combined with the white image.

As described above, according to the first embodiment, combining high-frequency components extracted from the $\lambda_{415}$ image with the relative intensities of the $\lambda_{415}$ image to the $\lambda_{630}$ image allows exhaustive extraction of absorption information indicating changes in absorption from the $\lambda_{415}$ image and minimizes failure of extraction. Thus, display of such absorption information in combination with a white image allows much information useful to users to be presented.

Note that, in step S115 (see FIG. 4) of the first embodiment, the inhibiting process is performed on the assumption that the values indicating the amounts of change in absorption are negative values. The process, however, may be performed using the values indicating the amounts of change in absorption as positive values by inverting positive/negative of the intensities of high-frequency components and the relative intensities or standardizing the intensities. In this case, a function of inhibiting a positive output value further as the absolute value in the addition result is larger may be used in step S115 described above. The inhibitory function, for example, has a form obtained by inverting the graph $I_{out}=f(|I_{add}|)$ illustrated in FIG. 6 with respect to an axis $|I_{add}|$.

First Modification of First Embodiment

Figure 7:
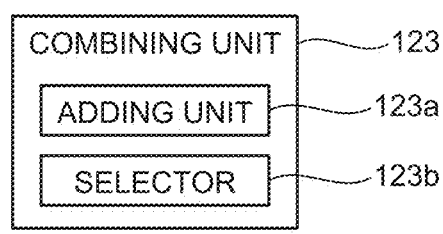
FIG. 7 is a schematic diagram illustrating a configuration of a combining unit included in an image processing device according to a first modification of the first embodiment.

Next, a first modification of the first embodiment will be described. FIG. 7 is a schematic diagram illustrating a configuration of a combining unit included in an image processing device according to the first modification. The image processing device according to the first modification includes a combining unit 123 illustrated in FIG. 7 instead of the combining unit 113 illustrated in FIG. 1.

The combining unit 123 includes an adding unit 123a configured at the intensity of a high-frequency component and the relative intensity, and a selector 123b configured to select a value of either of the intensity of the high-frequency component and the relative intensity. Note that the configurations and operations of the respective components of the computation unit other than the combining unit 123 and the configurations and operations of the respective components of the image processing device other than the computation unit are the same as those in the first embodiment.

Figure 8:
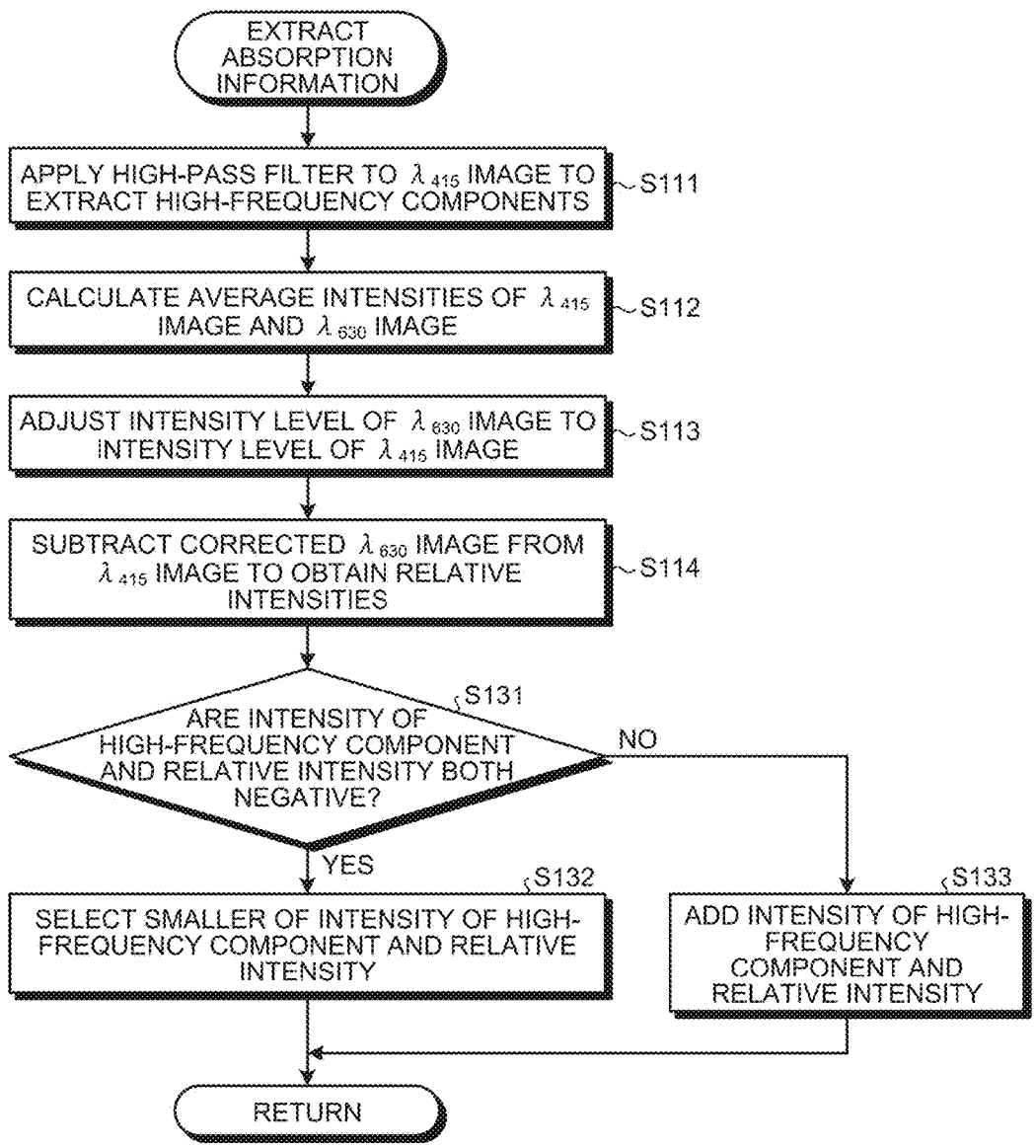
FIG. 8 is a flowchart illustrating a process of extracting absorption information in the first modification of the first embodiment.

FIG. 8 is a flowchart illustrating a process of extracting absorption information in the first modification. Note that steps S111 to S114 illustrated in FIG. 8 are the same as those in the first embodiment (see FIG. 4).

In step S131 subsequent to step S114, the combining unit 123 determines whether or not the intensity of a high-frequency component and the relative intensity at the same pixel positions are both negative among the intensities of the high-frequency components extracted in step S111 and the relative intensities calculated in step S114. As described above, since the value indicating the amount of change in absorption is a negative value, the intensity of the high-frequency component and the relative intensity at the same pixel position both being negative means that the change in absorption at the pixel position has been extracted as the high-frequency component and has also been extracted as the relative intensity.

If the intensity of the high-frequency component and the relative intensity are both negative (step S131: Yes), the selector 123b selects the smaller of the intensity of the high-frequency component and the relative intensity, that is, one having the larger absolute value so that the change in absorption is not doubly extracted (step S132). The selected value is output as absorption information.

If at least one of the intensity of the high-frequency component and the relative intensity is positive (step S131: No), the adding unit 123a adds the intensity of the high-frequency component and the relative intensity (step S133). The resulting addition value is output as absorption information. Thereafter, the process returns to the main routine.

As described above, according to the first modification, double extraction of a change in absorption is minimized with higher accuracy.

Note that, in the first modification described above, the process of inhibiting double extraction of changes in absorption is performed on the assumption that the values indicating the amounts of change in absorption are negative values. The process, however, may be performed using the values indicating the amounts of change in absorption as positive values by inverting positive/negative of the intensities of high-frequency components and the relative intensities or standardizing the intensities.

In this case, it is determined in step S131 of FIG. 8 whether or not the intensity of the high-frequency component and the relative intensity are both positive, and the absorption information is extracted in such a manner that the larger of the intensity of the high-frequency component and the relative intensity is selected if the intensities are both positive (see step S132) or that the intensity of the high-frequency component and the relative intensity are added if at least one of the intensities is negative (see step S133). In other words, if the positive/negative signs of the intensity of a high-frequency component and the relative intensity are both the same as that of the value indicating a change in absorption, one having the larger absolute value is selected; otherwise, an addition value of the intensity of the high-frequency component and the relative intensity is calculated.

Second Modification of First Embodiment

Next, a second modification of the first embodiment will be described. While the intensity of a high-frequency component extracted from the $\lambda_{415}$ image and the relative intensity between the $\lambda_{415}$ image and the $\lambda_{630}$ image are simply added for combination in the first embodiment described above, the intensity of a high-frequency component and the relative intensity may be each appropriately weighted before being added. In this case, since a fine change in absorption is low in visibility, a weight on the intensity of the high-frequency component is preferably set greater than that on the relative intensity.

Third Modification of First Embodiment

Next, a third modification of the first embodiment will be described. While the processing in the case where a plurality of narrow-band images are acquired has been described in the first embodiment, at least one narrow-band image is sufficient. For example, a narrow-band image having a center wavelength of 415 nm and a wide-band white image may be acquired, and R components of the pixel values of respective pixels constituting the white image may be used instead of the pixel values of the narrow-band image having a center wavelength of 630 nm in the first embodiment.

Second Embodiment

Figure 9:
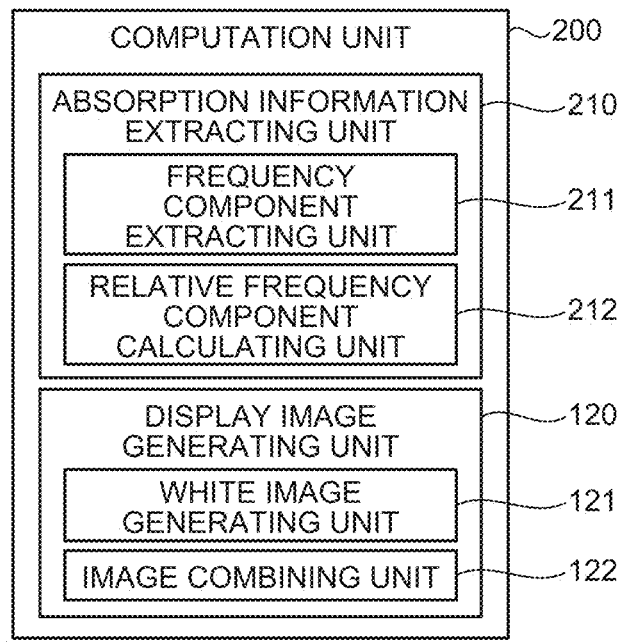
FIG. 9 is a block diagram illustrating a configuration of a computation unit included in an image processing device according to a second embodiment.

Next, a second embodiment will be described. FIG. 9 is a block diagram illustrating a configuration of a computation unit included in an image processing device according to the second embodiment. Note that the configurations and operations of the respective components of the image processing device other than the computation unit are the same as those in the first embodiment.

As illustrated in FIG. 9, a computation unit 200 included in the image processing device according to the second embodiment includes an absorption information extracting unit 210 and a display image generating unit 120. Among these components, the configuration and operation of the display image generating unit 120 are the same as those in the first embodiment.

The absorption information extracting unit 210 includes a frequency component extracting unit 211 configured to extract a specific frequency component in each narrow-band image, and a relative frequency component calculating unit 212 configured to calculate a relative intensity of the specific frequency component between a plurality of narrow-band images.

Next, operation of the image processing device according to the second embodiment will be described. The overall operation of the image processing device according to the second embodiment is similar to that in FIG. 2, but details of the process of extracting absorption information in step S11 are different from those in the first embodiment.

Figure 10:
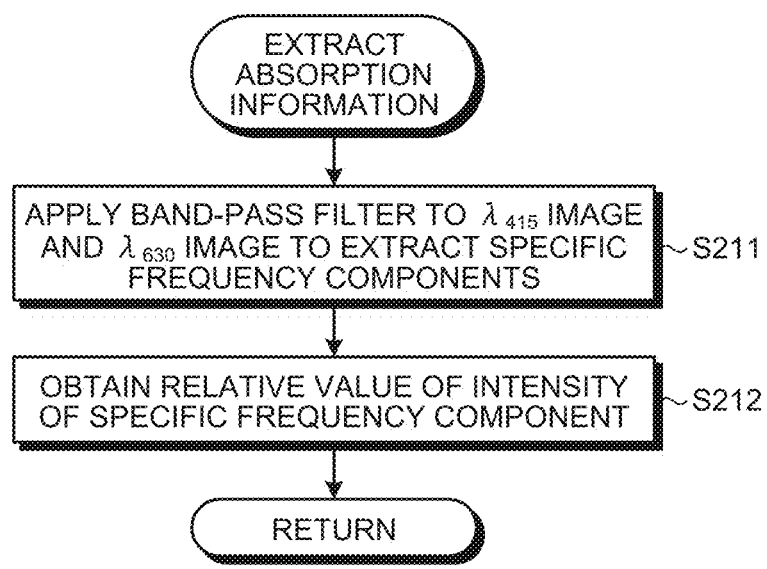
FIG. 10 is a flowchart illustrating a process of extracting absorption information in the second embodiment.

FIG. 10 is a flowchart illustrating a process of extracting absorption information in the second embodiment. In the following as well, a case of extracting absorption information from the $\lambda_{415}$ image will be described similarly to the first embodiment.

In step S211 subsequent to step S10 (see FIG. 2), the frequency component extracting unit 211 applies a band-pass filter to the $\lambda_{415}$ image and the $\lambda_{630}$ image to extract specific frequency components. The frequency components to be extracted are in a band wider toward the lower frequency than the high-pass filter used in the first embodiment so that a change in absorption of a relatively large region may also be extracted.

In a specific frequency component image generated by application of the band-pass filter to the $\lambda_{415}$ image, a regional change in absorption such as the absorption change region m13 also becomes easier to be extracted in addition to the fine blood vessels m11 and the slightly thicker blood vessels m12 as illustrated in FIG. 3. On the other hand, the band being widened toward the lower frequency also results in a possibility of extraction of a structure such as the shape of a mucosa.

In contrast, since a light absorber such as a blood vessel hardly appears in the $\lambda_{630}$ image, a structure such as the shape of a mucosa is mainly extracted in a specific frequency component image generated by application of a band-pass filter to the $\lambda_{630}$ image.

In subsequent step S212, the relative frequency component calculating unit 212 subtracts the intensity of a specific frequency component extracted from the $\lambda_{630}$ image from the intensity of the specific frequency component extracted from the $\lambda_{415}$ image to obtain a relative value of the intensity of the specific frequency component.

More specifically, an average value $Avg_{415}$ of pixel values of pixels in the original $\lambda_{415}$ image and an average value $Avg_{630}$ of pixel values of pixels in the original $\lambda_{630}$ image are first calculated. Note that the pixels whose pixel values are acquired may be all the pixels in each image or pixels in a predetermined region of interest. A ratio of the average values $Avg_{415}/Avg_{630}$ is then integrated with the pixel values of respective pixels in specific frequency component image based on the $\lambda_{630}$ image, so that correction is performed to adjust the intensity level of the specific frequency component image based on the $\lambda_{630}$ image to that of the specific frequency component image based on the $\lambda_{415}$ image. In this manner, the intensity levels of the specific frequency component images are made to be equal, and a relative value is then obtained by subtraction of a pixel value of the specific frequency component image based on the $\lambda_{630}$ image from a pixel value of the specific frequency component image based on the $\lambda_{415}$ image at the same pixel position.

This allows information indicating a structure such as the shape of a mucosa contained in the specific frequency component extracted from the $\lambda_{415}$ image to be removed. The absorption information extracting unit 210 outputs the relative value obtained by the subtracting process as absorption information. Thereafter, the process returns to the main routine.

As described above, according to the second embodiment, absorption information may be acquired through a simple computation process of extracting a specific frequency component from each of the $\lambda_{415}$ image and the $\lambda_{630}$ image and obtaining a relative value between the extracted specific frequency components.

Note that, in the second embodiment as well, a plurality of narrow-band images need not necessarily be acquired. For example, similarly to the third modification described above, a narrow-band image having a center wavelength of 415 nm and a wide-band white image may be acquired, and R components of the pixel values of respective pixels constituting the white image may be used instead of the pixel values of the narrow-band image having a center wavelength of 630 nm.

Third Embodiment

Figure 11:
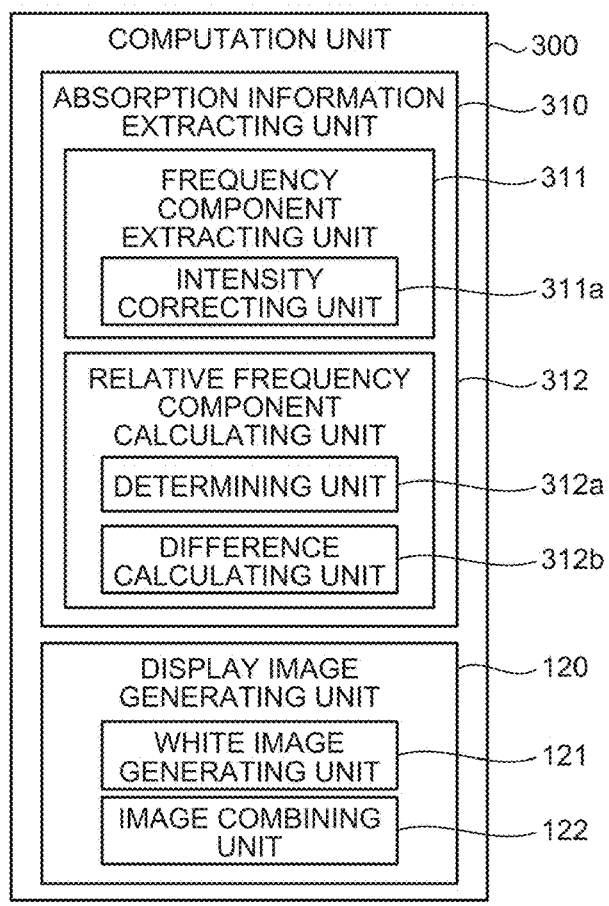
FIG. 11 is a block diagram illustrating a configuration of a computation unit included in an image processing device according to a third embodiment.

Next, a third embodiment will be described. FIG. 11 is a block diagram illustrating a configuration of a computation unit included in an image processing device according to the third embodiment. Note that the configurations and operations of the respective components of the image processing device other than the computation unit are the same as those in the first embodiment.

As illustrated in FIG. 11, a computation unit 300 included in the image processing device according to the third embodiment includes an absorption information extracting unit 310 and a display image generating unit 120. Among these components, the configuration and operation of the display image generating unit 120 are the same as those in the first embodiment.

The absorption information extracting unit 310 includes a frequency component extracting unit 311 configured to extract a specific frequency component in each narrow-band image, and a relative frequency component calculating unit 312 configured to calculate a relative intensity of the specific frequency component between a plurality of narrow-band images.

The frequency component extracting unit 311 includes an intensity correcting unit 311*a* configured to perform correction to make the intensity level of the first image and the intensity level the second image equal to each other.

The relative frequency component calculating unit 312 includes a determining unit 312*a* configured to determine whether or not the positive/negative signs of the specific frequency components in the first and second images are both the same as that of the value indicating a change in absorption, and a difference calculating unit 312*b* configured to calculate a difference between the specific frequency components in the first and second images.

Figure 12:
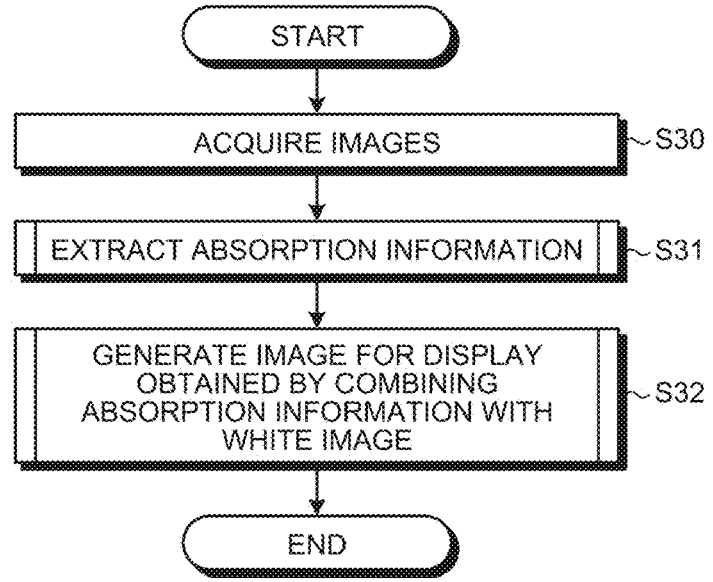
FIG. 12 is a flowchart illustrating operation of the image processing device according to the third embodiment.

Next, operation of the image processing device according to the third embodiment will be described. FIG. 12 is a flowchart illustrating the operation of the image processing device according to the third embodiment. The overall operation of the image processing device according to the third embodiment is similar to that in FIG. 2 of the first embodiment described above, and since steps S30 and S32 are the same processes as those of steps S10 and S12 in FIG. 2 of the first embodiment described above, the description thereof will not be repeated. In addition, in the following, a case of extracting absorption information from the $\lambda_{415}$ image will be described similarly to the first embodiment.

As illustrated in FIG. 12, the absorption information extracting unit 310 first extracts absorption information from the $\lambda_{415}$ image (step S31). As described above in the first embodiment, changes in absorption appear from a superficial layer under a mucosa to a middle layer in the $\lambda_{415}$ image. The changes in absorption include a change in absorption in common with that appearing in an image in a close wavelength band such as a $\lambda_{460}$ image. In addition, since the $\lambda_{460}$ image is included in a base image, which is generated by a process described later, the color of a blood vessel appearing in the base image may change when changes in absorption exhaustively extracted from the $\lambda_{415}$ image are combined with the base image. Thus, in the third embodiment, a relative intensity to the $\lambda_{460}$ image is used so that changes in absorption in common with those in the $\lambda_{460}$ image are excluded and changes in absorption appearing intensely only in the $\lambda_{415}$ image are extracted.

Figure 13:
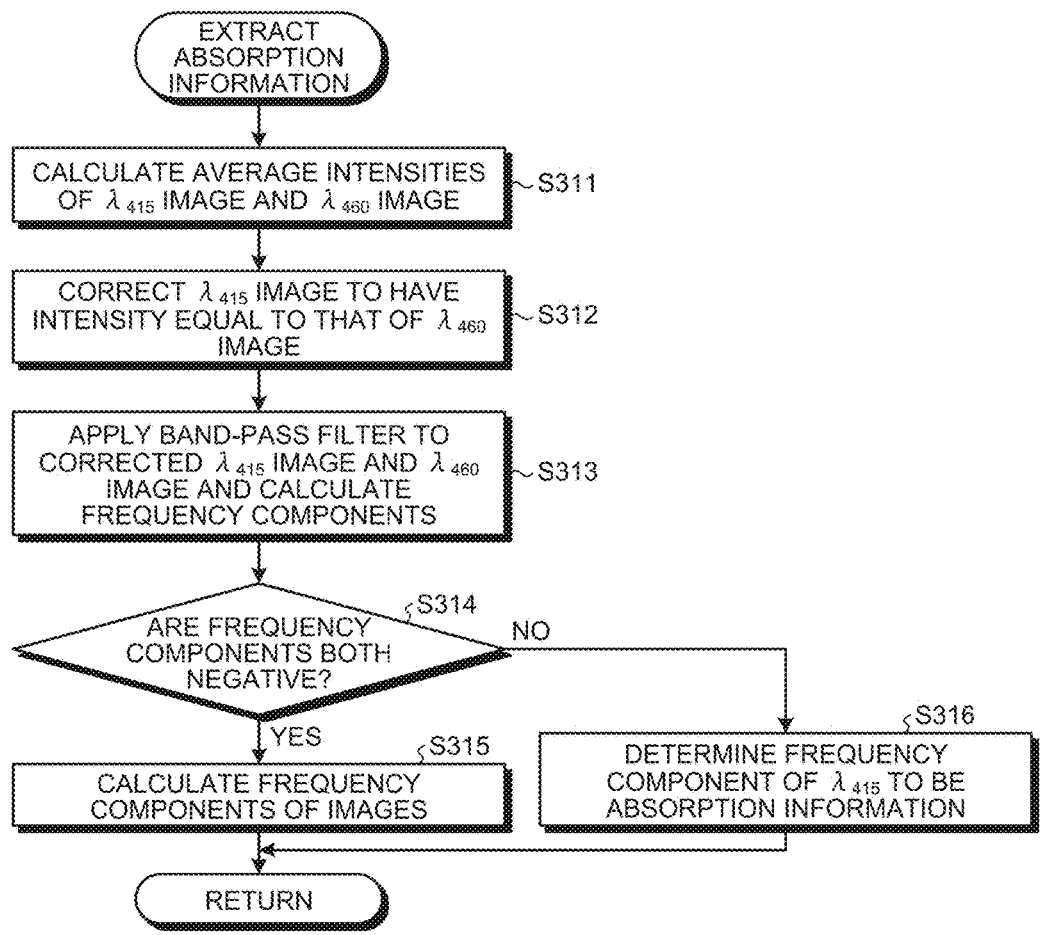
FIG. 13 is a flowchart illustrating an extraction process of extracting absorption information in FIG. 12.

FIG. 13 is a flowchart illustrating the extraction process of extracting absorption information in step S31 in FIG. 12.

As illustrated in FIG. 13, the intensity correcting unit 311a first calculates average intensities in the $\lambda_{415}$ image and the $\lambda_{460}$ image (hereinafter simply referred to as "the images") from the images (step S311).

Subsequently, the intensity correcting unit 311a performs correction to make the intensities (intensity levels) of the images become equal on the basis of the average intensities (step S312).

Thereafter, the frequency component extracting unit 311 calculates a frequency component from each of the images corrected by the intensity correcting unit 311a (step S313). Thereafter, as in the second embodiment described above, when the frequency component in the $\lambda_{460}$ image is subtracted from the frequency component in the $\lambda_{415}$ image, a change in absorption appearing only in the $\lambda_{460}$ image but not appearing in the $\lambda_{415}$ image appears as a positive amplitude in the difference image. Since the calculated difference image is combined as absorption information with the base image, a positive amplitude in the base image, if any, may offset the change in absorption in the base image and lower the contrast of a blood vessel. Thus, in the third embodiment, the subtraction is performed only in a region in which the frequency component in the $\lambda_{415}$ image and the frequency component in the $\lambda_{460}$ image are both negative, that is, changes in absorption appear in common in the $\lambda_{415}$ image and the $\lambda_{460}$ image. Specifically, the determining unit 312a determines whether or not the frequency components in the images are both negative (step S314). If the determining unit 312a determines that the frequency components in the images are both negative (step S314: Yes), the image processing device 1 proceeds to step S315, which will be described below. In contrast, if the determining unit 312a determines that at least one of the frequency components in the images is positive (step S314: No), the image processing device 1 proceeds to step S316, which will be described below.

In step S315, the difference calculating unit 312b calculates a difference between the frequency components of the images. After step S315, the image processing device 1 returns to the main routine in FIG. 12.

In step S316, the relative frequency component calculating unit 312 determines the frequency component in the $\lambda_{415}$ image to be absorption information. After step S316, the image processing device 1 returns to the main routine in FIG. 12.

According to the third embodiment described above, correlation between images in which sufficient absorption by hemoglobin is present is used, so that a change in absorption appearing intensely only in a specific narrow-band image may be extracted.

While the absorption information extracting unit 310 extracts absorption information by using a relative intensity to the $\lambda_{460}$ image in the third embodiment, another image corresponding to B (blue) to G (green) bands such as a $\lambda_{540}$ image may be used since a white image corresponding to B to G bands has similar absorption characteristics.

First Modification of Third Embodiment

Figure 14:
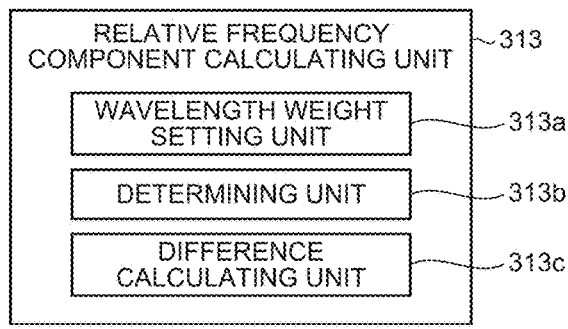
FIG. 14 is a block diagram illustrating a configuration of a frequency component extracting unit of a computation unit according to a first modification of the third embodiment.

Next, a first modification of the third embodiment will be described. FIG. 14 is a block diagram illustrating a configuration of a frequency component extracting unit of a computation unit according to the first modification. The image processing device according to the first modification includes a relative frequency component calculating unit 313 illustrated in FIG. 14 instead of the relative frequency component calculating unit 312 illustrated in FIG. 11.

The relative frequency component calculating unit 313 calculates a relative intensity of the specific frequency component between a plurality of narrow-band images. The relative frequency component calculating unit 313 includes a wavelength weight setting unit 313a configured to set weights on first and second images on the basis of the wavelength bands of light with which the first and second images are imaged, a determining unit 313b configured to determine whether or not the positive/negative signs of the specific frequency components in the first and second images are both the same as that of the value indicating a change in absorption, and a difference calculating unit 313c configured to calculate a difference between the specific frequency components in the first and second images on the basis of the weights set by the wavelength weight setting unit 313a. In the image processing device according to the first modification, the configurations and operations of the respective components of the computation unit other than the relative frequency component calculating unit 312 illustrated in FIG. 11 and the configurations and operations of the respective components of the image processing device other than the computation unit are the same as those in the third embodiment.

Figure 15:
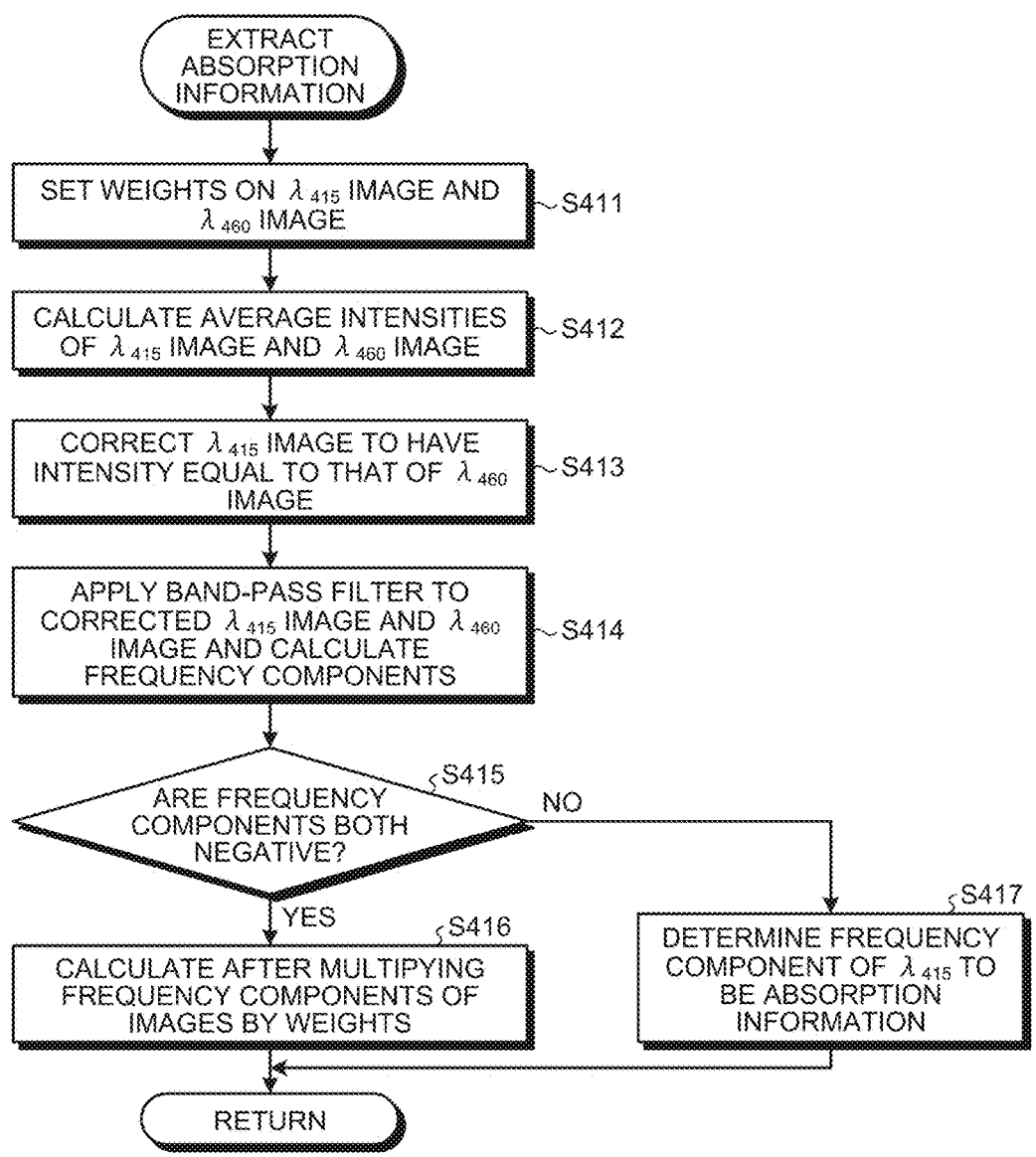
FIG. 15 is a flowchart illustrating an extraction process of extracting absorption information in the first modification of the third embodiment.

FIG. 15 is a flowchart illustrating an extraction process of extracting absorption information according to the first modification.

As illustrated in FIG. 15, the wavelength weight setting unit 313a first sets weights on the images (step S411). Specifically, since the amount light of $\lambda_{460}$ absorbed by hemoglobin is smaller than that of light of $\lambda_{415}$, when changes in absorption in common in the $\lambda_{460}$ image and in the $\lambda_{415}$ image are present, the amount of change appearing in the $\lambda_{460}$ image is likely to be smaller than that in the $\lambda_{415}$ image. Thus, the wavelength weight setting unit 313a sets weight on the images so that the weight on the $\lambda_{460}$ image is larger than that on the $\lambda_{415}$ image. The setting method is, for example, such that the wavelength weight setting unit 313a refers to a table indicating a weight coefficient for each wavelength recorded in the storage unit 50 to set a weight. Since steps S412 to S414 correspond to steps S311 to S313, respectively, in FIG. 13 described above, the description thereof will not be repeated.

In step S415, the determining unit 313b determines whether or not the frequency components in the images are both negative. If the determining unit 313b determines that the frequency components in the images are both negative (step S415: Yes), the image processing device 1 proceeds to step S416, which will be described below. In contrast, if the determining unit 313b determines that at least one of the frequency components in the images is positive (step S415: No), the image processing device 1 proceeds to step S417, which will be described below.

In step S416, the difference calculating unit 313c calculates a difference after multiplying the frequency components of the images by the weights. After step S416, the image processing device 1 returns to the main routine in FIG. 12.

In step S417, the difference calculating unit 313c determines the frequency component in the $\lambda_{415}$ image to be absorption information. After step S417, the image processing device 1 returns to the main routine in FIG. 12.

According to the first modification of the third embodiment described above, setting weights depending on the wavelength bands allows a change in absorption appearing intensely only in a specific narrow-band image to be extracted with higher accuracy.

Note that, while the wavelength weight setting unit 313a refers to the table indicating a weight coefficient for each wavelength recorded in the storage unit 50 to set a weight in the first modification of the third embodiment, weights based on average values of specific frequency components of the $\lambda_{460}$ image and the $\lambda_{415}$ image may be set or weights based on differences from the average values of the specific frequency components of the $\lambda_{460}$ image and the $\lambda_{415}$ image may be set. Needless to say, the wavelength weight setting unit 313a may use an exponentially increasing coefficient or a linearly increasing coefficient for weighting.

Second Modification of Third Embodiment

Figure 16:
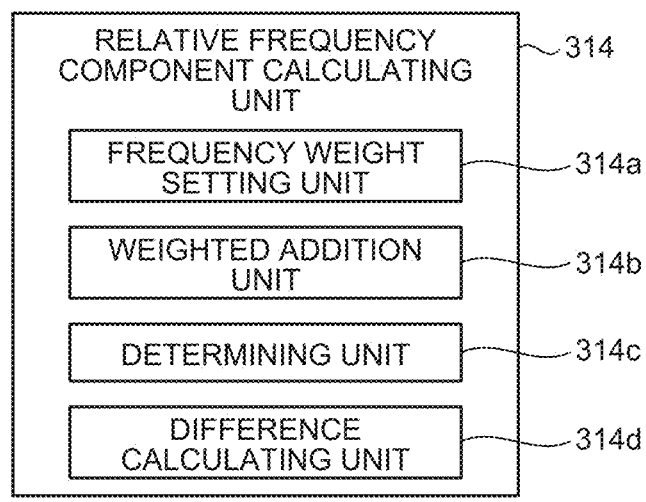
FIG. 16 is a block diagram illustrating a configuration of a frequency component extracting unit of a computation unit according to a second modification of the third embodiment.

Next, a second modification of the third embodiment will be described. FIG. 16 is a block diagram illustrating a configuration of a frequency component extracting unit of a computation unit according to the second modification. An image processing device according to the second modification includes a relative frequency component calculating unit 314 illustrated in FIG. 16 instead of the relative frequency component calculating unit 312 illustrated in FIG. 11.

The relative frequency component calculating unit 314 calculates a relative intensity of the specific frequency component between a plurality of narrow-band images. The relative frequency component calculating unit 314 includes a frequency weight setting unit 314a configured to set a weight on each of a plurality of frequency bands, a weighted addition unit 314b configured to add frequency components in a plurality of frequency bands in the first and second images on the basis of the weights set by the frequency weight setting unit 314a, a determining unit 314c configured to determine whether or not the positive/negative signs of the results of addition of the frequency components in the first and second images are both the same as that of the value indicating the change in absorption, and a difference calculating unit 314d configured to calculates a difference between the results of addition of the frequency components in the first and second images. In the image processing device according to the second modification, the configurations and operations of the respective components of the computation unit other than the relative frequency component calculating unit 312 illustrated in FIG. 11 and the configurations and operations of the respective components of the image processing device other than the computation unit are the same as those in the third embodiment.

Figure 17:
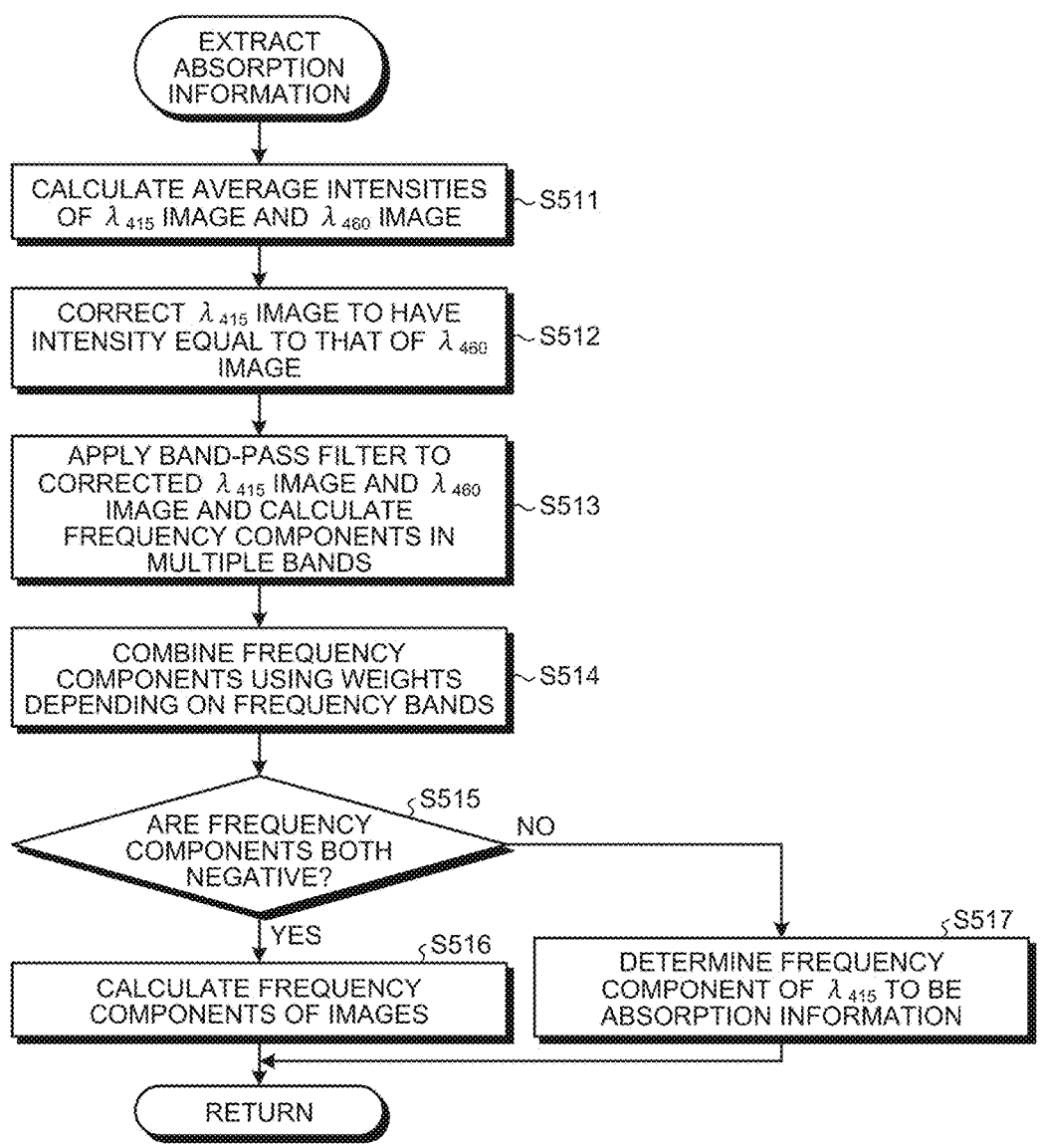
FIG. 17 is a flowchart illustrating an extraction process of extracting absorption information in the second modification of the third embodiment.

FIG. 17 is a flowchart illustrating an extraction process of extracting absorption information according to the second modification. Since steps S511 and S512 in FIG. 17 are the same processes as those in steps S311 and S312, respectively, in FIG. 13 described above, the description thereof will not be repeated.

In step S513, the frequency component extracting unit 311 calculates frequency components in a plurality of bands from the corrected images. As mentioned in the first embodiment, changes in absorption appear from a superficial layer under a mucosa to a middle layer in the $\lambda_{415}$ image, and among the changes in absorption, changes in absorption due to fine blood vessels appear in high-frequency components while regional changes in absorption appear in intermediate-frequency components. The amounts of change due to fine blood vessels, however, are likely to be smaller than those due to regional changes in absorption. For this reason, if frequency components in a band corresponding to high frequency to intermediate frequency are simply extracted, a high-frequency component may be hidden in an intermediate-frequency component and the amount of change due to a fine blood vessel may not be extracted. Thus, in the second modification, the frequency weight setting unit 314a sets weights depending on frequency bands, and combines respective frequency components calculated in S513 described above by using the set weights (step S514). The weights are set to be larger for higher frequency bands. For example, the frequency weight setting unit 314a refers to a table indicating a weight coefficient for each frequency recorded in the storage unit 50 to set a weight. Since steps S515 to S517 are the same processes as those in steps S314 to S316, respectively, in FIG. 13 described above, the description thereof will not be repeated.

According to the second modification of the third embodiment described above, setting weights depending on the frequency bands allows a change in absorption appearing intensely only in a specific narrow-band image to be extracted with higher accuracy.

Fourth Embodiment

Figure 18:
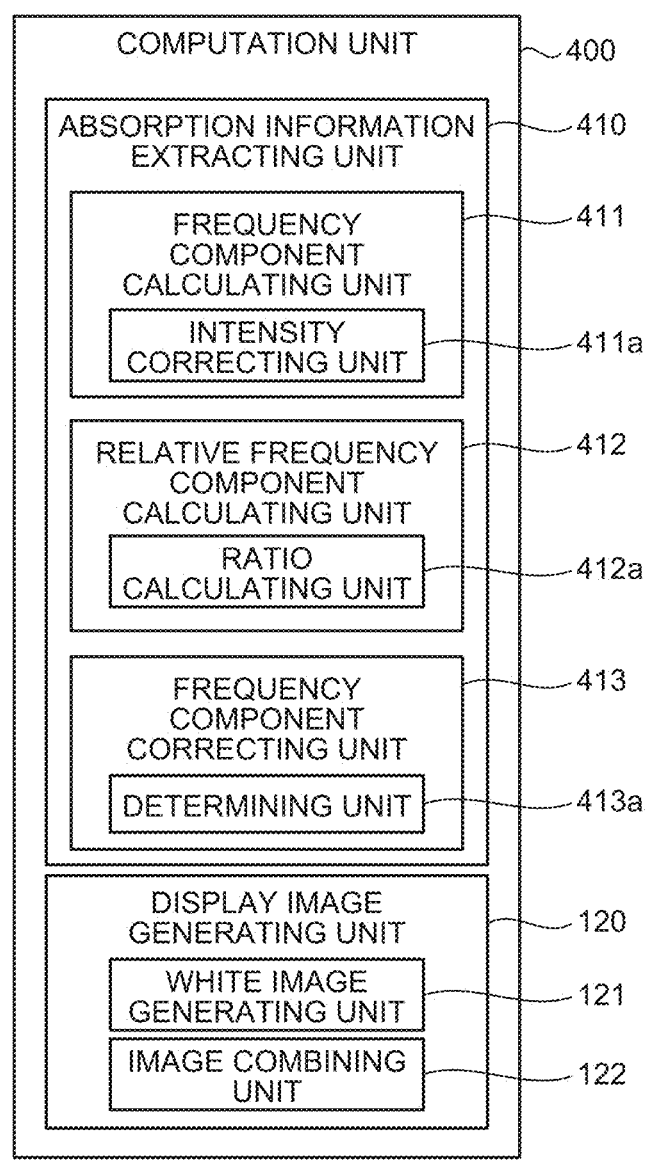
FIG. 18 is a block diagram illustrating a configuration of a computation unit included in an image processing device according to a fourth embodiment.

Next, a fourth embodiment is described. FIG. 18 is a block diagram illustrating a configuration of a computation unit included in an image processing device according to the fourth embodiment. Note that the configurations and operations of the respective components of the image processing device other than the computation unit are the same as those in the first embodiment.

As illustrated in FIG. 18, a computation unit 400 included in the image processing device according to the fourth embodiment includes an absorption information extracting unit 410 and a display image generating unit 120. Among these components, the configuration and operation of the display image generating unit 120 are the same as those in the first embodiment.

The absorption information extracting unit 410 includes a frequency component extracting unit 411 configured to extract a specific frequency component in each narrow-band image, a relative frequency component calculating unit 412 configured to calculate a relative intensity of the specific frequency component between a plurality of narrow-band images, and a frequency component correcting unit 413 configured to correct the intensity of a frequency component in a specific narrow-band image on the basis of the relative frequency component.

The frequency component extracting unit 411 includes an intensity correcting unit 411a configured to perform correction to make the intensity level of the first image and the intensity level of the second image equal to each other.

The relative frequency component calculating unit 412 includes a ratio calculating unit 412a configured to calculate a ratio of the specific frequency components in the first and second images.

The frequency component correcting unit 413 includes a determining unit 413a configured to determine whether or not the positive/negative signs of the specific frequency components in the first and second images are both the same as that of the value indicating a change in absorption.

Figure 19:
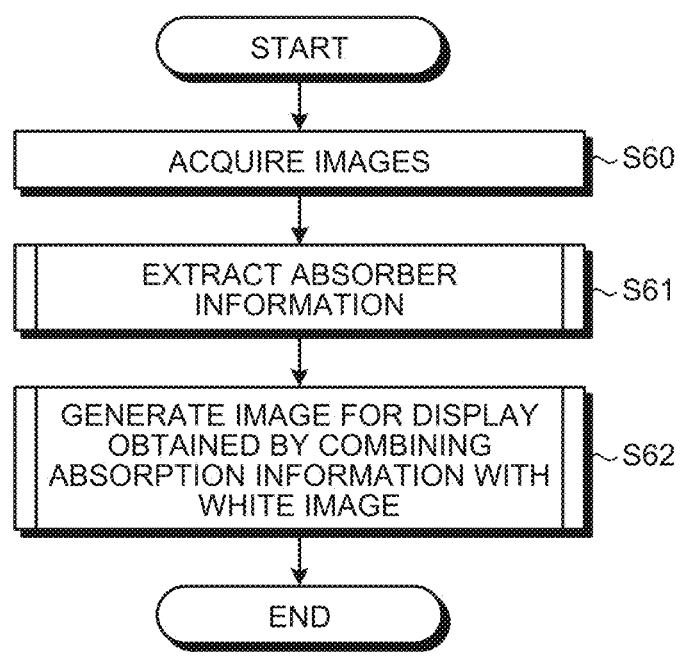
FIG. 19 is a flowchart illustrating operation of the image processing device according to the fourth embodiment.

Next, operation of the image processing device according to the fourth embodiment will be described. FIG. 19 is a flowchart illustrating the operation of the image processing device according to the fourth embodiment. The overall operation of the image processing device according to the fourth embodiment is similar to that in FIG. 2 of the first embodiment described above, and since steps S60 and S62 are the same processes as those of steps S10 and S12 in FIG. 2 of the first embodiment described above, the description thereof will not be repeated. In addition, in the following, a case of extracting absorption information from the $\lambda_{415}$ image will be described similarly to the first embodiment.

Figure 20:
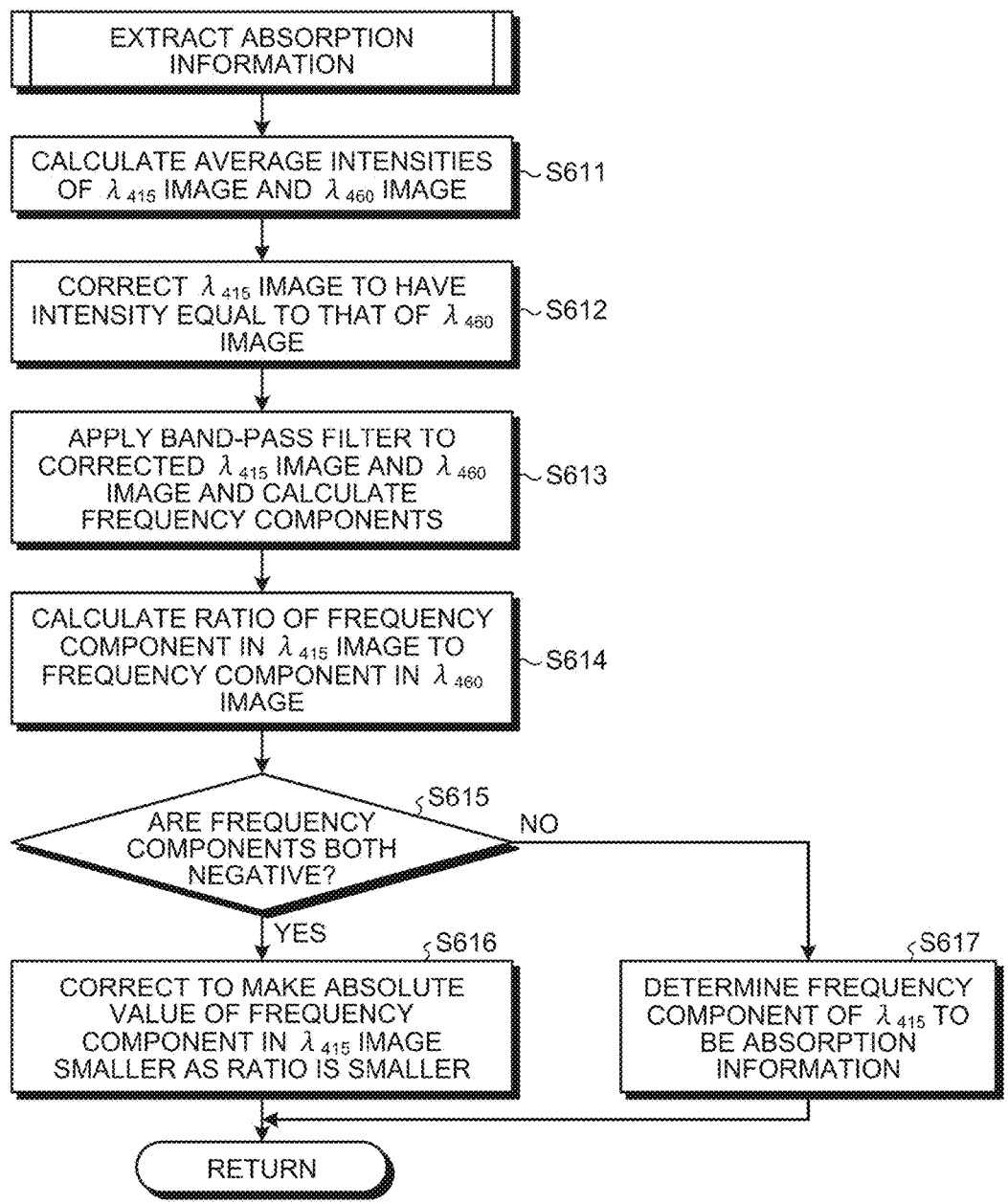
FIG. 20 is a flowchart illustrating an extraction process of extracting absorption information in FIG. 19.

FIG. 20 is a flowchart illustrating the extraction process of extracting absorption information in step S61 in FIG. 19.

As illustrated in FIG. 20, the intensity correcting unit 411a first calculates average intensities in the $\lambda_{415}$ image and the $\lambda_{460}$ image (hereinafter simply referred to as "the images") from the images (step S611).

Subsequently, the intensity correcting unit 411a performs correction to make the intensities (intensity levels) of the images become equal on the basis of the average intensities (step S612).

Thereafter, the frequency component extracting unit 411 calculates a frequency component from each of the images corrected by the intensity correcting unit 411a (step S613). The ratio calculating unit 412a then calculates a ratio of the frequency component in the $\lambda_{415}$ image to the frequency component in the $\lambda_{460}$ image (step S614). After calculation of the ratio, the determining unit 413a determines whether or not the frequency components in the images are both negative similarly to the third embodiment (step S615). If the determining unit 413a determines that the frequency components in the images are both negative (step S615: Yes), the image processing device 1 proceeds to step S616, which will be described below. In contrast, if the determining unit 413a determines that at least one of the frequency components in the images is positive (step S615: No), the image processing device 1 proceeds to step S617, which will be described below.

In step S616, the frequency component correcting unit 413 performs correction so that the absolute value of the frequency component in the $\lambda_{415}$ image becomes smaller as the ratio is smaller on the basis of the ratio calculated in step S614. The correction method includes referring to a coefficient table recorded in the storage unit 50, and multiplying the frequency component in the $\lambda_{415}$ image by the obtained coefficient, for example. After step S616, the image processing device 1 returns to the main routine in FIG. 19.

In step S617, the absorption information extracting unit 410 determines the frequency component in the $\lambda_{415}$ image to be absorption information. After step S617, the image processing device 1 returns to the main routine in FIG. 19.

According to the fourth embodiment described above, correlation between images in which sufficient absorption by hemoglobin is present is used to correct frequency components in a specific narrow-band image, so that a change in absorption appearing intensely only in the specific narrow-band image may be extracted.

First Modification of Fourth Embodiment

Figure 21:
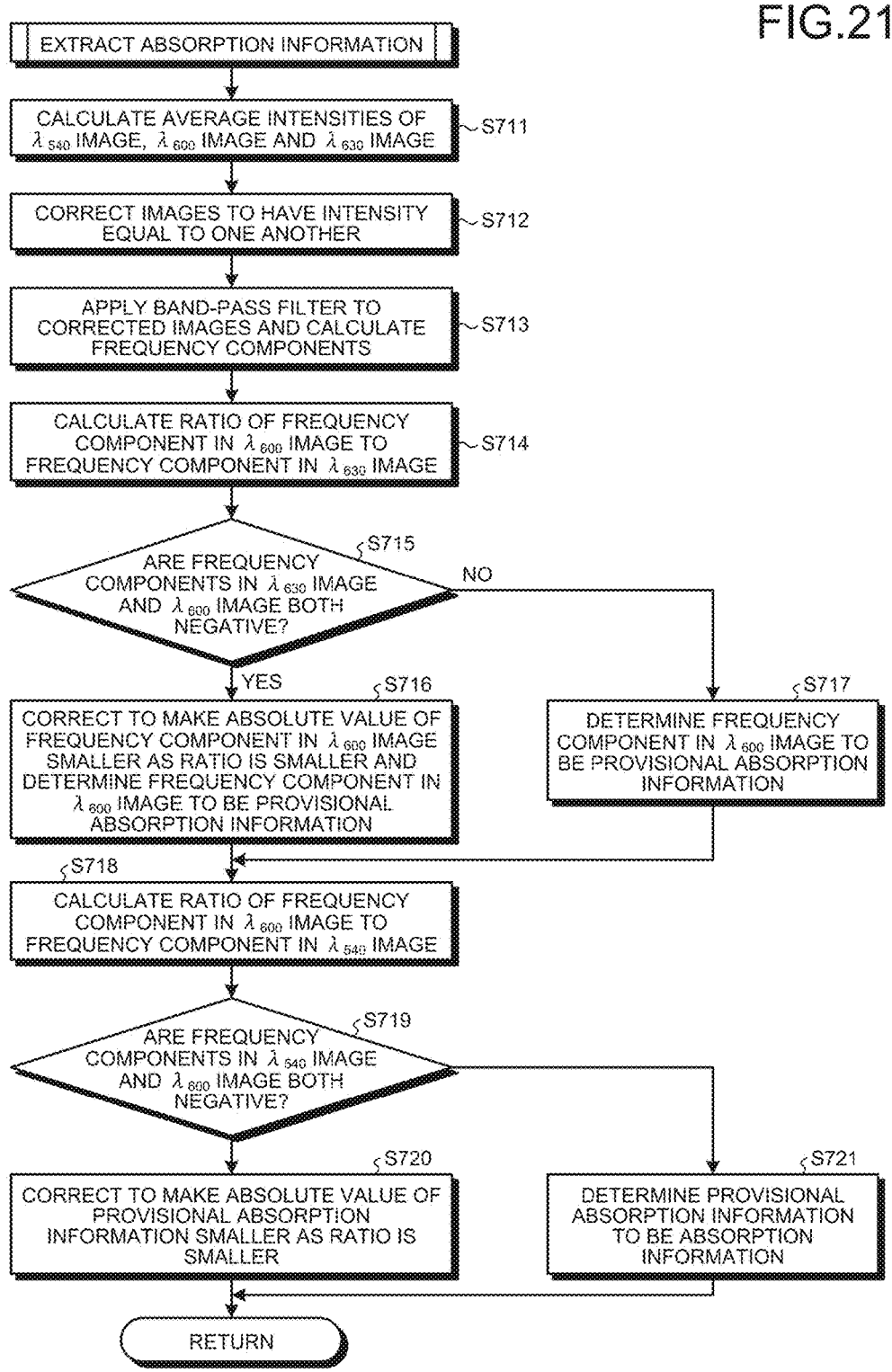
FIG. 21 is a flowchart illustrating an extraction process of extracting absorption information in a first modification of the fourth embodiment.

Next, a first modification of the fourth embodiment will be described. FIG. 21 is a flowchart illustrating an extraction process of extracting absorption information in the first modification. In addition, in the following, a case of extracting absorption information from a $\lambda_{600}$ image will be described.

As illustrated in FIG. 21, the intensity correcting unit 411a first calculates average intensities in the $\lambda_{540}$ image, the $\lambda_{600}$ image, and the $\lambda_{630}$ image from the images (step S711).

Subsequently, the intensity correcting unit 411a performs correction to make the intensities (intensity levels) of the $\lambda_{540}$ image, the $\lambda_{600}$ image, and the $\lambda_{630}$ image become equal on the basis of the average intensities (step S712).

Thereafter, the frequency component extracting unit 411 calculates frequency components from the $\lambda_{540}$ image, the $\lambda_{600}$ image, and the $\lambda_{630}$ image corrected by the intensity correcting unit 411a (step S713). The ratio calculating unit 412a then calculates a ratio of the frequency component in the $\lambda_{600}$ image to the frequency component in the $\lambda_{630}$ image (step S714). After calculation of the ratio, the determining unit 413a determines whether or not the frequency components in the $\lambda_{630}$ image and the $\lambda_{600}$ image are both negative (step S715). If the determining unit 413a determines that the frequency components in the $\lambda_{630}$ image and the $\lambda_{600}$ image are both negative (step S715: Yes), the image processing device 1 proceeds to step S716, which will be described below. In contrast, if the determining unit 413a determines that at least one of the frequency components in the $\lambda_{630}$ image and the $\lambda_{600}$ image is positive (step S715: No), the image processing device 1 proceeds to step S717, which will be described below.

In step S716, the frequency component correcting unit 413 performs correction so that the absolute value of the frequency component in the $\lambda_{600}$ image becomes smaller as the ratio is smaller on the basis of the ratio calculated in step S714, and determines the correction result to be provisional absorption information. The correction method includes referring to a coefficient table recorded in the storage unit 50, and multiplying the frequency component in the $\lambda_{600}$ image by the obtained coefficient, for example.

In step S717, the absorption information extracting unit 410 determines the frequency component in the $\lambda_{600}$ image to be provisional absorption information.

Subsequently, the ratio calculating unit 412a calculates a ratio of the frequency component in the $\lambda_{600}$ image to the frequency component in the $\lambda_{540}$ image (step S718). After calculation of the ratio, the determining unit 413a determines whether or not the frequency components in the $\lambda_{540}$ image and the $\lambda_{600}$ image are both negative (step S719). If the determining unit 413a determines that the frequency components in the $\lambda_{540}$ image and the $\lambda_{600}$ image are both negative (step S719: Yes), the image processing device 1 proceeds to step S720, which will be described below. In contrast, if the determining unit 413a determines that at least one of the frequency components in the $\lambda_{540}$ image and the $\lambda_{600}$ image is positive (step S719: No), the image processing device 1 proceeds to step S721, which will be described below.

In step S720, the frequency component correcting unit 413 performs correction so that the absolute value of the provisional absorption information becomes smaller as the ratio is smaller on the basis of the ratio calculated in step S718, and determines the correction result to be absorption information. The correction method includes referring to a coefficient table recorded in the storage unit 50, and multiplying the provisional absorption information by the obtained coefficient, for example. After step S720, the image processing device 1 returns to the main routine in FIG. 19.

In step S721, the absorption information extracting unit 410 determines the provisional absorption information to be absorption information. After step S721, the image processing device 1 returns to the main routine in FIG. 19.

According to the first modification of the fourth embodiment, a plurality of correlations between images are used to correct frequency components in a specific narrow-band image, so that a change in absorption appearing intensely only in the specific narrow-band image may be extracted with higher accuracy.

The first to fourth embodiments, the first to third modifications of the first embodiment, the first and second modifications of the third embodiment, and the first modification of the fourth embodiment described above may be achieved by executing image processing programs stored in a storage device on a computer system such as a personal computer or a work station. In addition, such a computer system may be used while being connected with devices such as another computer system and a server via a local area network (LAN), a wide area network (WAN), or a public line such as the Internet. In this case, the image processing devices according to the first to fourth embodiments, the first to third modifications of the first embodiment, the first and second modifications of the third embodiment, and the first modification of the fourth embodiment may acquire image data of intraluminal images via the network, output a result of image processing to various output devices (such as a viewer or a printer) connected via the network, and store a result of image processing to a storage device (such as a storage medium and a reader therefor) connected via the network.

The present disclosure is not limited to first to fourth embodiments, the first to third modifications of the first embodiment, the first and second modifications of the third embodiment, and the first modification of the fourth embodiment, but the components disclosed in the embodiments and modifications may be appropriately combined to achieve various inventions. For example, some of the components presented in the embodiments and modifications may be excluded, or components presented in different embodiments or modifications may be appropriately combined.

According to the present disclosure, use of a specific frequency component in a first image that is a narrow-band image and correlation between the first image and a second image allows changes in absorption of various shapes and sizes to be exhaustively extracted and minimizes extraction of structures such as the shape of a mucosa, which allows generation of an image for display that does not affect the visibility when changes in absorption extracted from the narrow-band image are combined with another image.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An image processing device comprising:
a processor comprising hardware, wherein the processor is configured to:
  acquire a plurality of images comprising:
    a first image that is a narrow-band image; and
    a second image having a wavelength component distribution that is different from a wavelength component distribution of the first image;
  extract absorption information from the first image on the basis of:
    a specific frequency component in the first image; and
    correlation between intensity of the first image and intensity of the second image,
    wherein the absorption information is image information indicating a change in absorption caused by absorption of narrow-band light used in capturing of the first image by a light absorber; and
  generate an image for display by combining the absorption information with at least any one of the plurality of images.

2. The image processing device according to claim 1, wherein the second image is a narrow-band image captured with light that is less absorbed by the light absorber than the narrow-band light used in capturing of the first image.

3. The image processing device according to claim 1, wherein the processor, in extracting the absorption information, is configured to:
  extract the specific frequency component in the first image;
  calculate a relative intensity between the first image and the second image; and
  combine an intensity of the specific frequency component extracted with the relative intensity calculated.

4. The image processing device according to claim 3, wherein the processor, in calculating the relative intensity between the first image and the second image, is configured to:
  perform correction to make an intensity level of the first image and an intensity level of the second image equal to each other; and
  obtain the relative intensity by subtracting image intensities between the first image and the second image resulting from the correction of the intensity levels.

5. The image processing device according to claim 3, wherein the processor, in combining the intensity of the specific frequency component extracted with the relative intensity calculated, is configured to add an intensity of the specific frequency component and the relative intensity at a same pixel position.

6. The image processing device according to claim 5, wherein the absorption information includes a pixel position at which the change in absorption occurs and a value indicating an amount of change in absorption at the pixel position, and
wherein the processor, in combining the intensity of the specific frequency component extracted with the relative intensity calculated, is configured to inhibit an output value further as an absolute value in a result of addition by the processor is larger.

7. The image processing device according to claim 3, wherein the absorption information includes a pixel position at which the change in absorption occurs and a value indicating an amount of change in absorption at the pixel position, and wherein the processor, in combining the intensity of the specific frequency component extracted with the relative intensity calculated, is configured to:
  add an intensity of the specific frequency component and the relative intensity at a same pixel position;
  select either of the intensity of the specific frequency component and the relative intensity at the same pixel position; and
  output a result of selection when positive/negative signs of the intensity of the specific frequency component and the relative intensity are both identical to a sign of the value indicating the amount of change in absorption, or output a result of addition when the positive/negative signs of the intensity of the specific frequency component and the relative intensity are different from each other or when the positive/negative signs of the intensity of the specific frequency component and the relative intensity are both different from the sign of the value indicating the amount of change in absorption.

8. The image processing device according to claim 7, wherein the processor, in selecting either of the intensity of the specific frequency component and the relative intensity at the same pixel position, is configured to select one of the intensity of the specific frequency component and the relative intensity having the larger absolute value.

9. The image processing device according to claim 1, wherein the processor, in extracting the absorption information from the first image, is configured to:
  extract the specific frequency component in each of the first image and the second image; and
  calculate a relative value of an intensity of the specific frequency component in the first image to an intensity of the specific frequency component in the second image.

10. The image processing device according to claim 1, wherein the plurality of images comprises a plurality of narrow-band images corresponding to respective wavelength bands of R, G, and B, and
wherein the processor, in generating the image for display, is configured to:
  generate a white image on the basis of the narrow-band images; and
  combine the absorption information with the white image.

11. The image processing device according to claim 1, wherein the plurality of images comprises a white image, and
wherein the processor, in generating the image for display, is configured to combine the absorption information with the white image.

12. The image processing device according to claim 1, wherein the plurality of images are images acquired by capturing of an inside of a lumen of a living body.

13. The image processing device according to claim 9, wherein the processor, in calculating the relative value of the intensity of the specific frequency component in the first image to the intensity of the specific frequency component in the second image, is configured to calculate a difference between the specific frequency components in the first image and the second image.

14. The image processing device according to claim 13, wherein the processor is configured to:
  determine whether or not positive/negative signs of the specific frequency components in the first image and the second image are both identical to a sign of the value indicating the change in absorption; and
  calculate the difference only in a region in which the signs are determined to be both identical.

15. The image processing device according to claim 13, wherein the processor is configured to:
  set weights on the first image and the second image on the basis of wavelength bands of light used in capturing the first image and the second image; and
  calculate a difference between the frequency components in the first image and the second image on the basis of the weights set.

16. The image processing device according to claim 13, wherein the processor is configured to:
  divide the specific frequency component into a plurality of frequency bands for calculation;
  set a weight for each of the frequency bands;
  add frequency components in the frequency bands in the first image and the second image on the basis of the weights set; and
  calculate a difference between the frequency components in the first image and the second image resulting from addition.

17. The image processing device according to claim 9, wherein the processor is configured to correct an intensity of the frequency component in the first image on the basis of the relative frequency component.

18. The image processing device according to claim 17, wherein the processor is configured to calculate a ratio of the specific frequency components in the first image and the second image.

19. The image processing device according to claim 17, wherein the processor is configured to calculate a plurality of relative frequency components on the basis of frequency components in the first image and in an image other than the first image by further using one or more images in addition to the first image and the second image.

20. The image processing device according to claim 19, wherein the processor is configured to:
  determine whether or not positive/negative signs of the frequency components in the first image and in the image other than the first image are both identical to a sign of the value indicting the change in absorption; and
  perform the correction only in a region in which the signs are determined to be both identical.

21. The image processing device according to claim 9, wherein the processor is configured to perform correction to make an intensity level of the first image and an intensity level of the second image equal to each other.

22. An image processing method comprising:
acquiring a plurality of images comprising:
  a first image that is a narrow-band image; and
  a second image having a wavelength component distribution that is different from a wavelength component distribution of the first image;
extracting absorption information from the first image on the basis of:
  a specific frequency component in the first image; and
  correlation between intensity of the first image and intensity of the second image,
  wherein the absorption information is image information indicating a change in absorption caused by absorption of narrow-band light used in capturing of the first image by a light absorber; and generating an image for display by combining the absorption information with at least any one of the plurality of images.

23. A non-transitory computer-readable recording medium with an executable program stored thereon, the program causing a processor to execute:
acquiring a plurality of images comprising:
a first image that is a narrow-band image; and
a second image having a wavelength component distribution that is different from a wavelength component distribution of the first image;
extracting absorption information from the first image on the basis of:
a specific frequency component in the first image; and
correlation between intensity of the first image and intensity of the second image,
wherein the absorption information is image information indicating a change in absorption caused by absorption of narrow-band light used in capturing of the first image by a light absorber; and
generating an image for display by combining the absorption information with at least any one of the plurality of images.

* * * * *